US012608034B2

(12) United States Patent
Lu et al.

(10) Patent No.: US 12,608,034 B2
(45) Date of Patent: Apr. 21, 2026

(54) MASTER MANIPULATOR DEVICES FOR ROBOTS AND ROBOTS THEREOF

(71) Applicant: WUHAN UNITED IMAGING SURGICAL CO., LTD., Wuhan (CN)

(72) Inventors: Zhuangzhuang Lu, Wuhan (CN); Longquan Zhu, Wuhan (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 209 days.

(21) Appl. No.: 18/363,683

(22) Filed: Aug. 1, 2023

(65) Prior Publication Data

US 2023/0376066 A1    Nov. 23, 2023

Related U.S. Application Data

(63) Continuation of application No. PCT/CN2022/075243, filed on Jan. 30, 2022.

(30) Foreign Application Priority Data

| | | |
|---|---|---|
| Feb. 1, 2021 | (CN) .......................... | 202110135533.0 |
| Apr. 26, 2021 | (CN) .......................... | 202110454699.9 |
| Jul. 2, 2021 | (CN) .......................... | 202110752647.X |

(51) Int. Cl.
| | |
|---|---|
| *A61B 34/00* | (2016.01) |
| *B25J 13/02* | (2006.01) |
| *G05G 9/047* | (2006.01) |

(52) U.S. Cl.
CPC ............ *G05G 9/047* (2013.01); *B25J 13/025* (2013.01); *A61B 34/70* (2016.02);
(Continued)

(58) Field of Classification Search
CPC ............ A61B 34/70; G05G 9/00; B25J 13/00
See application file for complete search history.

(56) References Cited

U.S. PATENT DOCUMENTS

| | | | |
|---|---|---|---|
| 4,732,353 A | 3/1988 | Studer | |
| 6,377,011 B1 | 4/2002 | Ben-Ur | |

(Continued)

FOREIGN PATENT DOCUMENTS

| | | |
|---|---|---|
| CN | 101261781 A | 9/2008 |
| CN | 101444431 A | 6/2009 |

(Continued)

OTHER PUBLICATIONS

The Extended European Search Report in European Application No. 22745370.1 mailed on May 8, 2024, 7 pages.
(Continued)

*Primary Examiner* — Lynsey C Eiseman
(74) *Attorney, Agent, or Firm* — Poseidon Advanced IP LLC

(57) ABSTRACT

The present disclosure provides a master manipulator device for a robot. The master manipulator device comprises an end control assembly and a posture adjustment member. The posture adjustment member includes a first rotation mechanism and a second rotation mechanism. The first rotation mechanism is connected to the end control assembly, and the second rotation mechanism is connected to the first rotation mechanism. The end control assembly drives the first rotation mechanism to rotate around a rotation axis of the first rotation mechanism, and the end control assembly also drives the first rotation mechanism and the second rotation mechanism to rotate around a rotation axis of the second rotation mechanism.

20 Claims, 11 Drawing Sheets

(52) U.S. Cl.

CPC .............. *G05G 2009/0477* (2013.01); *G05G 2009/04774* (2013.01); *G05G 2505/00* (2013.01)

(56) References Cited

U.S. PATENT DOCUMENTS

| | | | |
|---|---|---|---|
| 6,429,849 | B1 | 8/2002 | An et al. |
| 2002/0040217 | A1 | 4/2002 | Jinno |
| 2008/0154246 | A1 | 6/2008 | Nowlin et al. |
| 2012/0053701 | A1 | 3/2012 | Yi et al. |
| 2016/0059409 | A1 | 3/2016 | Nawrat et al. |
| 2016/0374772 | A1 | 12/2016 | Hasegawa et al. |
| 2017/0151028 | A1 | 6/2017 | Ogawa et al. |
| 2018/0154521 | A1 | 6/2018 | Bosscher et al. |
| 2018/0353246 | A1 | 12/2018 | Ishihara et al. |
| 2019/0192247 | A1* | 6/2019 | Woo ...................... A61B 34/37 |
| 2019/0350662 | A1 | 11/2019 | Huang et al. |
| 2020/0015917 | A1 | 1/2020 | Cavalier et al. |
| 2020/0054378 | A1 | 2/2020 | Kincaid et al. |
| 2020/0289230 | A1 | 9/2020 | Denlinger et al. |
| 2020/0294423 | A1 | 9/2020 | Blain et al. |
| 2020/0356174 | A1 | 11/2020 | Andreff et al. |

FOREIGN PATENT DOCUMENTS

| | | | |
|---|---|---|---|
| CN | 102208150 | A | 10/2011 |
| CN | 103386687 | A | 11/2013 |
| CN | 103565529 | A | 2/2014 |
| CN | 104622585 | A | 5/2015 |
| CN | 104669299 | A | 6/2015 |
| CN | 104690708 | A | 6/2015 |
| CN | 105108762 | A | 12/2015 |
| CN | 105662589 | A | 6/2016 |
| CN | 106667583 | A | 5/2017 |
| CN | 107361848 | A | 11/2017 |
| CN | 107496031 | A | 12/2017 |
| CN | 107595395 | A | 1/2018 |
| CN | 108852514 | A | 11/2018 |
| CN | 109620367 | A | 4/2019 |
| CN | 109620413 | A | 4/2019 |
| CN | 109621330 | A | 4/2019 |
| CN | 110464470 | A | 11/2019 |
| CN | 110623710 | A | 12/2019 |
| CN | 209790401 | U | 12/2019 |
| CN | 210019449 | U | 2/2020 |
| CN | 111110353 | A | 5/2020 |
| CN | 111407409 | A | 7/2020 |
| CN | 111449758 | A | 7/2020 |
| CN | 111604874 | A | 9/2020 |
| CN | 111839740 | A | 10/2020 |
| CN | 112338939 | A | 2/2021 |
| CN | 112349191 | | 2/2021 |
| CN | 113116519 | A | 7/2021 |
| CN | 113208738 | A | 8/2021 |
| CN | 215265162 | U | 12/2021 |
| GB | 1263424 | A | 2/1972 |
| KR | 20200037637 | A | 4/2020 |
| WO | 2018112227 | A2 | 6/2018 |
| WO | 2019058336 | A1 | 3/2019 |
| WO | 2020188391 | A1 | 9/2020 |
| WO | 2020218678 | A1 | 10/2020 |
| WO | 2021128525 | A1 | 7/2021 |

OTHER PUBLICATIONS

The Extended European Search Report in European Application No. 22745368.5 mailed on May 8, 2024, 8 pages.
Partial Supplementary European Search Report in European Application No. 22745369.3 mailed on May 22, 2024, 12 pages.
International Search Report in PCT/CN2022/075243 mailed on May 7, 2022, 8 pages.
Written Opinion in PCT/CN2022/075243 mailed on May 7, 2022, 10 pages.
International Search Report in PCT/CN2022/075244 mailed on Apr. 14, 2022, 7 pages.
Written Opinion in PCT/CN2022/075244 mailed on Apr. 14, 2022, 10 pages.
International Search Report in PCT/CN2022/075245 mailed on May 5, 2022, 10 pages.
Written Opinion in PCT/CN2022/075245 mailed on May 5, 2022, 12 pages.
First Office Action in Chinese Application No. 202110752647.X mailed on Jun. 14, 2025, 22 pages.
The Second Office Action in Chinese Application No. 202110135533.0 mailed on Aug. 6, 2025, 22 pages.

* cited by examiner

200

1000

230

MASTER MANIPULATOR DEVICES FOR ROBOTS AND ROBOTS THEREOF

CROSS-REFERENCE TO RELATED APPLICATIONS

This application is a Continuation of International Application No. PCT/CN2022/075243, filed on Jan. 30, 2022, which claims priority to Chinese Application No. 202110135533.0, filed on Feb. 1, 2021, Chinese Application No. 202110454699.9, filed on Apr. 26, 2021, and Chinese Application No. 202110752647.X, filed on Jul. 2, 2021, the contents of which are incorporated herein by reference.

TECHNICAL FIELD

The present disclosure relates to the technical field of a medical device, and in particular, to a master manipulator device for a robot and a robot thereof.

BACKGROUND

In recent years, X-ray computed tomography (CT) imaging has made great progress in basic technologies and new clinical applications. Nowadays, CT is used in conjunction with various clinical departments to achieve a variety of examinations and treatments with remarkable medical effects, which is no longer just an imaging examination. CT image-guided surgical operations are performed on the premise of CT imaging, so that a situation can be judged in real time and adjustments can be made to the surgical operations in a timely manner, thereby significantly improving a surgical success rate, reducing a surgical risk, and improving a recovery speed and a quality of life of patients. However, a CT device uses X-rays, y rays, or the like, to perform the imaging. Performing surgery near the CT device will expose doctors to a radiation environment for a long period of time, thereby posing a great risk to health of the doctors. Accordingly, a master-slave teleoperated robot is created. The doctors are effectively protected from radiation exposure by controlling an image-guided robot to perform surgical operations via a remote operation. However, the current master-slave teleoperated robot is unable to simulate a posture of a doctor of operating and controlling surgical tools, which increases the surgical risk and an uncertainty of the surgical operations, thereby increasing an operation time, reducing an efficiency of the surgical operations, and affecting a success rate of the surgical operations. Therefore, it is desirable to provide a master-slave teleoperated robot, which simulates a posture of a doctor of operating and controlling surgical tools.

SUMMARY

An aspect of the present disclosure provides a master manipulator device for a robot. The master manipulator device comprises an end control assembly and a posture adjustment member. The posture adjustment member includes a first rotation mechanism and a second rotation mechanism. The first rotation mechanism is connected to the end control assembly, and the second rotation mechanism is connected to the first rotation mechanism. The end control assembly may drive the first rotation mechanism to rotate around a rotation axis of the first rotation mechanism, and the end control assembly may drive the first rotation mechanism and the second rotation mechanism to rotate around a rotation axis of the second rotation mechanism.

In some embodiments, the first rotation mechanism may include a first rotation shaft, a first installation base, and a second installation base. The end control assembly may be fixedly provided on the first installation base, the first installation base may be fixedly connected to the first rotation shaft, and the first rotation shaft may be rotatably provided on the second installation base. The second rotation mechanism may include a second rotation shaft and a third installation base. The second rotation shaft may be rotatably provided on the third installation base, and the second rotation shaft may be fixedly connected to the second installation base. An angle between a rotation axis of the first rotation shaft and a rotation axis of the second rotation shaft may be greater than 10°.

In some embodiments, the angle between the rotation axis of the first rotation shaft and the rotation axis of the second rotation shaft may be greater than 85°.

In some embodiments, the rotation axis of the first rotation shaft may intersect with the rotation axis of the second rotation shaft.

In some embodiments, the second rotation shaft may include a first portion and a second portion that are rotatable around the rotation axis of the second rotation shaft. The first portion and the second portion may be capable of rotating synchronously, and the second installation base may be provided between the first portion and the second portion such that the first rotation shaft and the second rotation shaft are located in a same plane.

In some embodiments, the master manipulator device may further include a first information acquisition device configured to detect a rotation angle of the first rotation mechanism and transmit the rotation angle of the first rotation mechanism to a communication device, and a second information acquisition device configured to detect a rotation angle of the second rotation mechanism and transmit the rotation angle of the second rotation mechanism to the communication device.

In some embodiments, the first information acquisition device may include a first encoder, and the second information acquisition device may include a second encoder.

In some embodiments, the master manipulator device may further include a first feedback assembly configured to apply a first posture adjustment resistance to the first rotation mechanism based on first feedback information, and a second feedback assembly configured to apply a second posture adjustment resistance to the second rotation mechanism based on second feedback information.

In some embodiments, an end portion of the first rotation shaft may be connected to the first feedback assembly. The first feedback assembly may include a first speed reduction assembly and a first feedback motor. The first feedback motor may be connected to the first rotation shaft through the first speed reduction assembly. An end portion of the second rotation shaft may be connected to the second feedback assembly. The second feedback assembly may include a second speed reduction assembly and a second feedback motor. The second feedback motor may be connected to the second rotation shaft through the second speed reduction assembly.

In some embodiments, the first speed reduction assembly may include a first synchronous wheel and a second synchronous wheel. A radius of the first synchronous wheel may be greater than a radius of the second synchronous wheel. The first synchronous wheel may be provided at the end of the first rotation shaft, and the second synchronous wheel may be provided at an output end of the first feedback motor. The first synchronous wheel may be in transmission connection with the second synchronous wheel. The second speed reduction assembly may include a third synchronous wheel and a fourth synchronous wheel. A radius of the third synchronous wheel may be greater than a radius of the fourth synchronous wheel. The third synchronous wheel may be provided at the end of the second rotation shaft, the fourth synchronous wheel being provided at an output end of the second feedback motor, and the third synchronous wheel may be in transmission connection with the fourth synchronous wheel.

In some embodiments, the first synchronous wheel may be in double-rope transmission connection with the second synchronous wheel, and the third synchronous wheel may be in double-rope transmission connection with the fourth synchronous wheel.

In some embodiments, the first rotation mechanism may include a posture adjustment base and a posture adjustment ring. The posture adjustment base may be rotatably connected to the posture adjustment ring, and the posture adjustment ring may be fixedly connected to the end control assembly. The second rotation mechanism may include a third rotation shaft. The third rotation shaft may be fixedly connected to the posture adjustment base. An angle between a rotation axis of the posture adjustment ring and the rotation axis of the second rotation shaft may be greater than 10°.

In some embodiments, an angle between the rotation axis of the posture adjustment ring and a rotation axis of the third rotation shaft may be greater than 85°.

In some embodiments, the rotation axis of the posture adjustment ring may intersect with the rotation axis of the third rotation shaft.

In some embodiments, the master manipulator device may further include a third information acquisition device configured to detect a rotation angle of the first rotation mechanism and transmit the rotation angle of the first rotation mechanism to a communication device, and a fourth information acquisition device configured to detect a rotation angle of the second rotation mechanism and transmit the rotation angle of the second rotation mechanism to the communication device.

In some embodiments, the third information acquisition device may include a third encoder, and the fourth information acquisition device may include a fourth encoder.

In some embodiments, the master manipulator device may further include a third feedback assembly configured to apply a third posture adjustment resistance to the first rotation mechanism based on third feedback information, and a fourth feedback assembly configured to apply a fourth posture adjustment resistance to the second rotation mechanism based on fourth feedback information.

In some embodiments, the third feedback assembly may include a third feedback motor. The third feedback motor may be fixedly connected to the posture adjustment ring or the posture adjustment base. The fourth feedback assembly may include a fourth feedback motor. The fourth feedback motor may be fixedly connected to the third rotation shaft.

In some embodiments, the posture adjustment member may further include a locking mechanism.

In some embodiments, the locking mechanism may include a first brake member configured to lock or unlock a rotation of the first rotation mechanism, and a second brake member configured to lock or unlock a rotation of the second rotation mechanism.

In some embodiments, the locking mechanism may include a plurality of electromagnets and a plurality of state detection units corresponding to the plurality of electromagnets. The plurality of electromagnets may be provided along a peripheral side of the end control assembly, and the plurality of state detection units may be configured to detect states of the plurality of electromagnets and transmit the states of the plurality of electromagnets to a communication device. The plurality of electromagnets may be connected to the end control assembly by energizing the plurality of electromagnets, thereby locking a posture of the end control assembly. The plurality of electromagnets may be disconnected from the end control assembly by de-energizing the plurality of electromagnets, thereby unlocking the posture of the end control assembly In some embodiments, the posture adjustment member may further include a plurality of posture adjustment touch switches. The plurality of posture adjustment touch switches may be provided along the peripheral side of the end control assembly.

In some embodiments, the posture adjustment member may further include a plurality of inclination detection members. The plurality of inclination detection members may be provided along the peripheral side of the end control assembly. The plurality of inclination detection members may be configured to detect an inclination angle of the end control assembly and transmit the inclination angle of the end control assembly to the communication device.

In some embodiments, the master manipulator device may further include a base. The base may include a base body and a rotation platform. The rotation platform may be fixedly connected to the second rotation mechanism of the posture adjustment member, and the rotation platform may be rotatably connected to the base body. A rotation plane of the rotation platform may be parallel, relative to the base body, to a plane in which the base body is located, and the rotation platform may be associated with a motion of at least one joint of the robot.

In some embodiments, the base may further include a drive member and a transmission assembly. The drive member may drive the rotation platform to rotate through the transmission assembly.

In some embodiments, the transmission assembly may include a worm and a worm gear meshed with each other. The worm may be connected to an output end of the drive member and the worm gear may be fixedly connected to the rotation platform.

In some embodiments, the transmission assembly may include a driving wheel and a driven wheel. The driving wheel and the driven wheel may be sleeved with a synchronous belt. The driving wheel may be connected to the output end of the drive member, and the driven wheel may be fixedly connected to the rotation platform.

In some embodiments, the rotation platform may be provided with a fifth encoder configured to detect a rotation angle of the rotation platform and transmit the rotation angle of the rotation platform to a communication device.

In some embodiments, the end control assembly may include an end control force feedback assembly configured to apply, based on end control force feedback information, a resistance to the end control assembly.

In some embodiments, the end control assembly may include at least one of a puncture needle assembly, a surgical cutting assembly, or a suture assembly.

Another aspect of the present disclosure provides a robot. The robot comprises a robot body, an end executor, and the master manipulator device as claimed above. The end executor may be connected to the robot body, the robot body may be electrically connected to a communication device, and the master manipulator device may be electrically connected to the communication device and the end executor.

BRIEF DESCRIPTION OF THE DRAWINGS

The present disclosure is further illustrated in terms of exemplary embodiments. These exemplary embodiments are described in detail with reference to the drawings. These embodiments are not limited, in these embodiments, the same numeral denotes the same structure, wherein.

DETAILED DESCRIPTION

Figure 1:
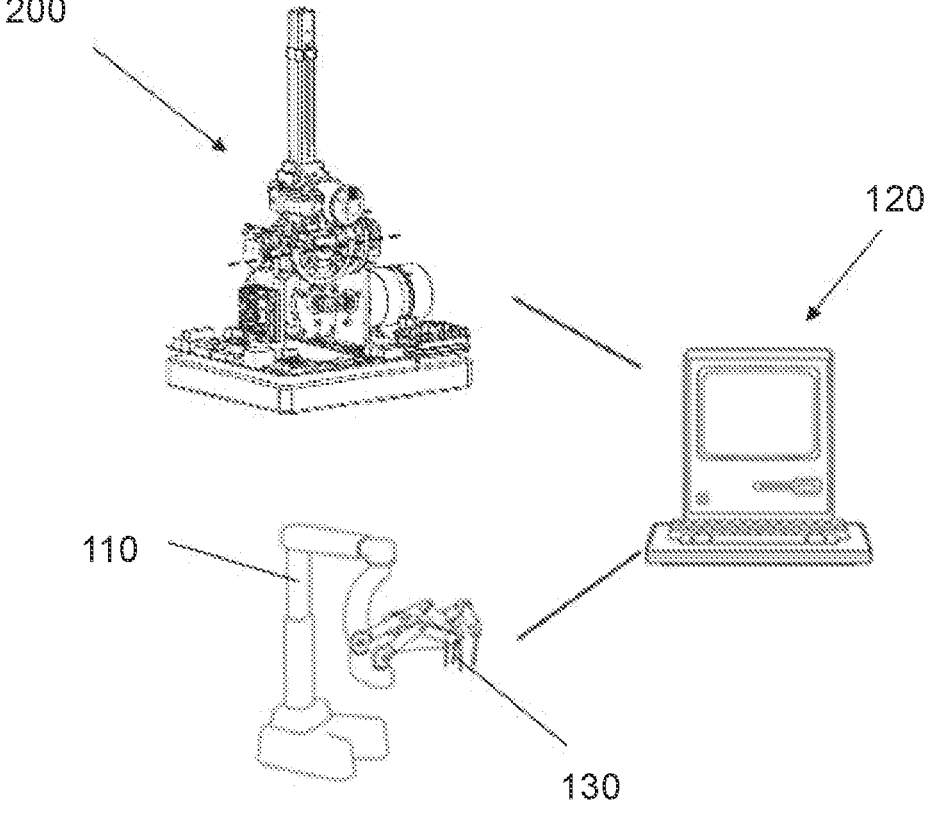
FIG. 1 is a schematic diagram illustrating an exemplary application scenario of a robot according to some embodiments of the present disclosure.

In order to more clearly illustrate the technical solutions of the embodiments of the present disclosure, the following will briefly introduce the drawings that need to be used in the description of the embodiments. Obviously, the accompanying drawings in the following description are only some examples or embodiments of the present disclosure, for those ordinary skilled in the art, the present disclosure can also be applied to other similar scenarios according to these drawings without any creative effort. Unless obviously obtained from the context or the context illustrates otherwise, the same numeral in the drawings refers to the same structure or operation.

It will be understood that the terms "system," "device," "unit," and/or "module" used herein are one method to distinguish different components, elements, parts, sections, or assemblies of different levels. However, words may be replaced by other expressions if they serve the same purpose.

As shown in the present disclosure and the claims, unless the context clearly suggests exceptional circumstances, the words "a", "an" and/or "the" do not specifically refer to the singular, but may also include the plural. Generally speaking, the terms "comprise" and "include" only imply that the clearly identified steps and elements are included, and these steps and elements do not constitute an exclusive list, and the method or device may also include other steps or elements.

Based on a continued advancement of technological research and product development in medical robots, a surgical robot has become one of the key fields in the medical robots category. The surgical robot is a medical device that integrates many disciplines such as clinical medicine, biomechanics, mechanics, computer science, microelectronics, or the like. With a clear imaging system and flexible mechanical arm, the surgical robot assists doctors in performing complex surgical operations in a form of minimally invasive surgery to complete an operation such as intraoperative positioning, cutting, puncturing, hemostasis, suturing, or the like. Under a guidance of CT imaging equipment, a medical staff uses the surgical robot to assist in surgical treatment. However, a surgery performed near the CT device will expose the medical staff to a radiation environment for a long period of time, thereby posing a significant risk to the health of the medical staff. Therefore, a master-slave teleoperated robot is used to control an image-guided robot to perform surgical operations via teleoperation. Current robots usually can not accurately simulate an operation process of the medical staff and provide feedback on force levels. A lack of force perception by the medical staff increases a surgical risk and an uncertainty of the surgical operations and affect a surgical efficiency.

To solve problems mentioned above, some embodiments of the present disclosure provide a robot for surgical operations. The robot may include a master manipulator device configured to operate an end executor of the robot. The master manipulator device may be capable of simulating the operation of a medical staff and providing force feedback to avoid risks involved in a surgical process and improve the surgical efficiency.

FIG. 1 is a schematic diagram illustrating an exemplary application scenario of a robot according to some embodiments of the present disclosure. As shown in FIG. 1, the robot may include a robot body 110, an end executor 130, and a master manipulator device 200. The end executor 130 is connected to the robot body 110 (e.g., provided at an end portion of a robot arm of the robot body 110), the robot body 110 is electrically connected to a communication device 120, and the master manipulator device 200 is electrically connected to the communication device 120 and the end executor 130, thereby controlling the end executor 130 to perform a synchronous operation.

When the robot is in actual use, the robot body 110 is located in a scanning room. Optionally, the robot body 110 includes a robotic arm capable of driving the end executor 130 installed at the end portion of the robotic arm to move, thereby adjusting a posture of a functional component at the end portion of the robotic arm. The end executor 130 is provided on the robot body 110. The end executor 130 is configured to perform the synchronous operation (e.g., puncturing, suturing, etc.). A control room is located adjacent to the scanning room, or there may be a distance between the control room and the scanning room. The control room is provided with an operation table of an imaging equipment. A concrete wall exists between the control room and the scanning room to shield rays. In addition, the master manipulator device 200 is provided in the control room. A doctor operates the master manipulator device 200 in the control room to control the robot body 110 in the scanning room, thereby completing a master-slave teleoperated surgical operation.

Figure 2:
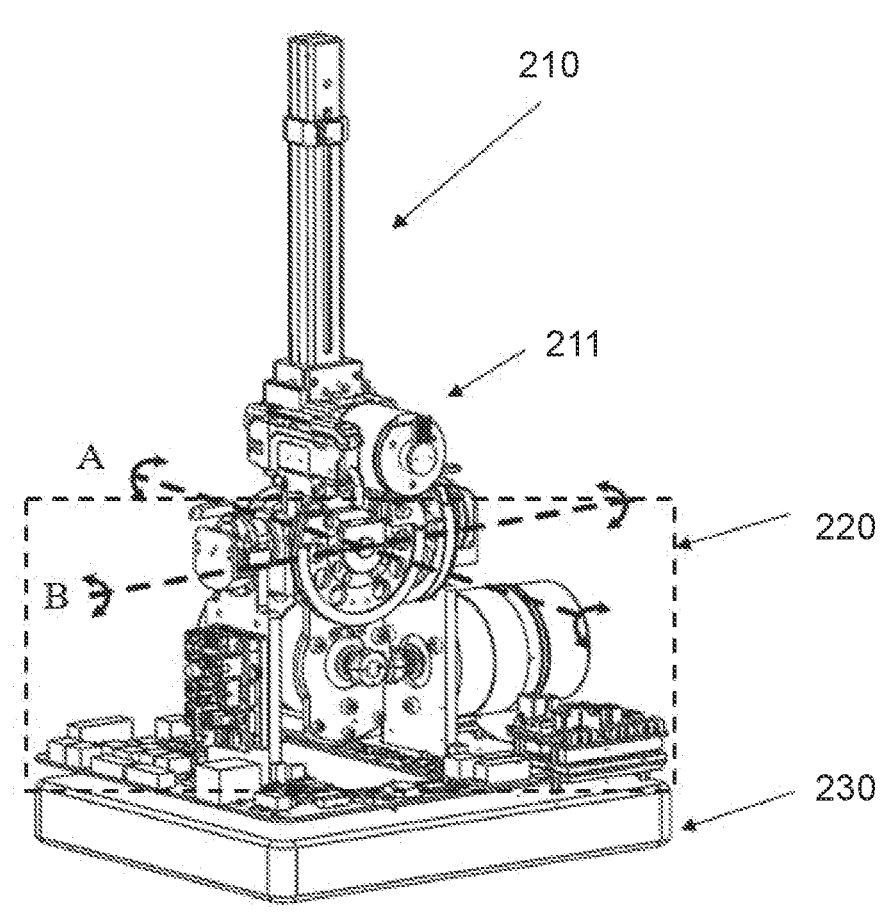
FIG. 2 is a schematic diagram illustrating an exemplary structure of a master manipulator device according to some embodiments of the present disclosure.

FIG. 2 is a schematic diagram illustrating an exemplary structure of a master manipulator device 200 according to some embodiments of the present disclosure. Detailed descriptions of the master manipulator device 200 illustrated in the embodiments of the present disclosure are provided below. It should be noted that the following embodiments are merely intended to illustrated the present disclosure, which are not limitations thereof.

As shown in FIG. 2, the master manipulator device 200 for a robot may include an end control assembly 210 and a posture adjustment member 220.

The end control assembly 210 is used to control the end executor 130 to perform operations, such as puncturing, suturing, etc. In some embodiments, the end control assembly 210 may be a hollow column structure that is easy to be held. In some embodiments, an adaptive design may be performed on the end control assembly 210 according to operation habits of a medical staff and a structure of the end executor 130. For example, the end control assembly 210 may be accordingly provided as a puncture needle assembly, a surgical cutting assembly, a suture assembly, etc., depending on different end executors 130 (e.g., a puncture needle, a surgical cutting, a suture needle, etc.). A shape of the end control assembly 210 may be provided to correspond to a shape of a functional component or another shape that is convenient for operation, which is not limited herein.

In some embodiments, the end control assembly 210 includes an end control force feedback assembly, and the end control force feedback assembly applies, based on end control force feedback information, a resistance to the end control assembly 210. The end control force feedback information may include a magnitude and a direction of the resistance, etc. In some embodiments, the end executor 130 may be a puncture needle. When the puncture needle is inserted into a patient, a body tissue exerts a reaction force on the puncture needle, i.e., a resistance to puncture, which is detected by a sensor provided on the end executor 130.

In some embodiments, when the end control assembly 210 controls the end executor 130 (e.g., the puncture needle) to perform an operation, a puncture resistance encountered by the puncture needle may be fed back to the robot body 110. The robot body 110 may control the end control force feedback assembly to apply a resistance equivalent to the puncture resistance to the end control assembly 210. In this way, the medical staff can feel an insertion resistance of the puncture needle through the puncture resistance fed back by the end control force feedback assembly during the puncture operation, thereby achieving a real simulation of performing the puncture by holding the puncture needle.

In some embodiments, the end control force feedback assembly may include an execution motor and a position detection unit. The position detection unit may be used to detect a current position state of a slider, identify a motion stroke of the slider, and feed back the current position state and the motion stroke to the robot body 110. For example, during the execution of the puncture by the puncture needle, the robot body 110 controls the execution motor to apply a certain current to produce a torque action. A resistance generated by the torque is consistent to an actual insertion resistance of the puncture needle. The resistance is applied to the hands of the medical staff via a slip ring on the end control assembly 210, and the medical staff feels a resistance when moving the slip ring, thereby achieving a feedback function of a puncture force.

When the slip ring of the end control assembly 210 is in a linear motion, the end control force feedback assembly is able to detect a distance of the linear motion of the slip ring and feedback the distance to the robot body 110. The robot body 110 may convert the distance of the linear motion of the slip ring into a linear displacement and control the robotic arm to drive the puncture needle to perform the puncture operation through the linear displacement. For example, the end control force feedback assembly may be connected to a roller of a linear motion assembly. When the roller rotates, the end control force feedback assembly is able to detect the distance of the linear motion of the slip ring and feedback the distance to the robot body 110 to control the puncture needle for the puncture operation.

In some embodiments, the master manipulator device 200 may be electrically connected to the communication device 120 and the end executor 130, and the communication device 120 may be electrically connected to the robot body 110. Merely by way of example, resistance information to the end executor 130 may be transmitted to the robot body 110. The robot body 110 may send corresponding force feedback information to the master manipulator device 200 via the communication device 120 based on the resistance information, thereby achieving a signal transmission. In some embodiments, connection manners of the communication device 120, the master manipulator 200, and the robot body 110 may include a wired connection, a wireless connection, or a combination thereof. The wired connection may include a connection via cables, fiber optic cables, telephone lines, or the like, or any combination thereof. The wireless connection may include a connection via Bluetooth, Wi-Fi, WiMax, WLAN, ZigBee, mobile networks (e.g., 3G, 4G, 5G, etc.), or the like, or any combination thereof.

Figure 3:
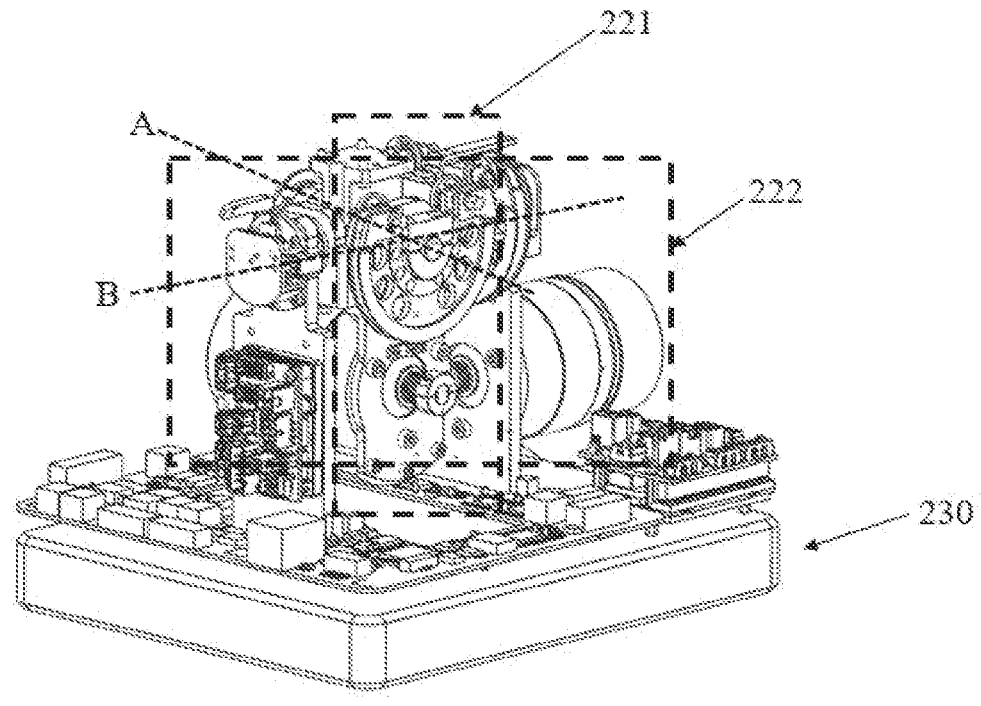
FIG. 3 is a schematic diagram illustrating an exemplary structure of a posture adjustment member according to some embodiments of the present disclosure.

FIG. 3 is a schematic diagram illustrating an exemplary structure of a posture adjustment member 220 according to some embodiments of the present disclosure. As shown in FIG. 3, the posture adjustment member 220 is a device used to adjust the posture of the end control assembly 210. In some embodiments, the posture adjustment member 220 may include a first rotation mechanism 221 and a second rotation mechanism 222. The first rotation mechanism 221 is connected to the end control assembly 210. The second rotation mechanism 222 is connected to the first rotation mechanism 221. The end control assembly 210 drives the first rotation mechanism 221 to rotate around a rotation axis A of the first rotation mechanism 221. That is, a motion of the first rotation mechanism 221 driven by the end control assembly 210 has no effect on the second rotation mechanism 222. The end control assembly 210 drives the first rotation mechanism 221 and the second rotation mechanism 222 to rotate around a rotation axis B of the second rotation mechanism 222. That is, when the end control assembly 210 drives the posture adjustment member 220 to rotate around the rotation axis B of the second rotation mechanism 222, the first rotation mechanism 221 and the second rotation mechanism 222 as a whole rotate around the rotation axis B of the second rotation mechanism 222.

In some embodiments, a motion of the end control assembly 210 in a first direction corresponds to a first rotation-freedom degree of the first rotation mechanism 221. A motion of the end control assembly 210 and the first rotation mechanism 221 as a whole in a second direction corresponds to a second rotation-freedom degree of the second rotation mechanism 222. A rotation motion of the first rotation mechanism 221 does not affect the second rotation mechanism 222. However, a rotation of the second rotation mechanism 222 is able to drive a direction of the rotation axis A of the first rotation mechanism 221 to be changed. An actual adjusted amount of posture motion of the end control assembly 210 is a vector sum superimposed by the rotations of the first rotation mechanism 221 and the second rotation mechanism 222. In a specific embodiment, the first rotation mechanism 221 may be connected to a bottom of the end control assembly 210, and the motion of the end control assembly 210 in the first direction is capable of driving the first rotation mechanism 221 to rotate around the rotation axis A of the first rotation mechanism 221. When the end control assembly 210 moves in the second direction, the end control assembly 210 and the first rotation mechanism 221 may be considered as a whole with a fixed relative position, which is capable of driving the second rotation mechanism 222 to rotate around the rotation axis B of the second rotation mechanism 222.

Figure 4:
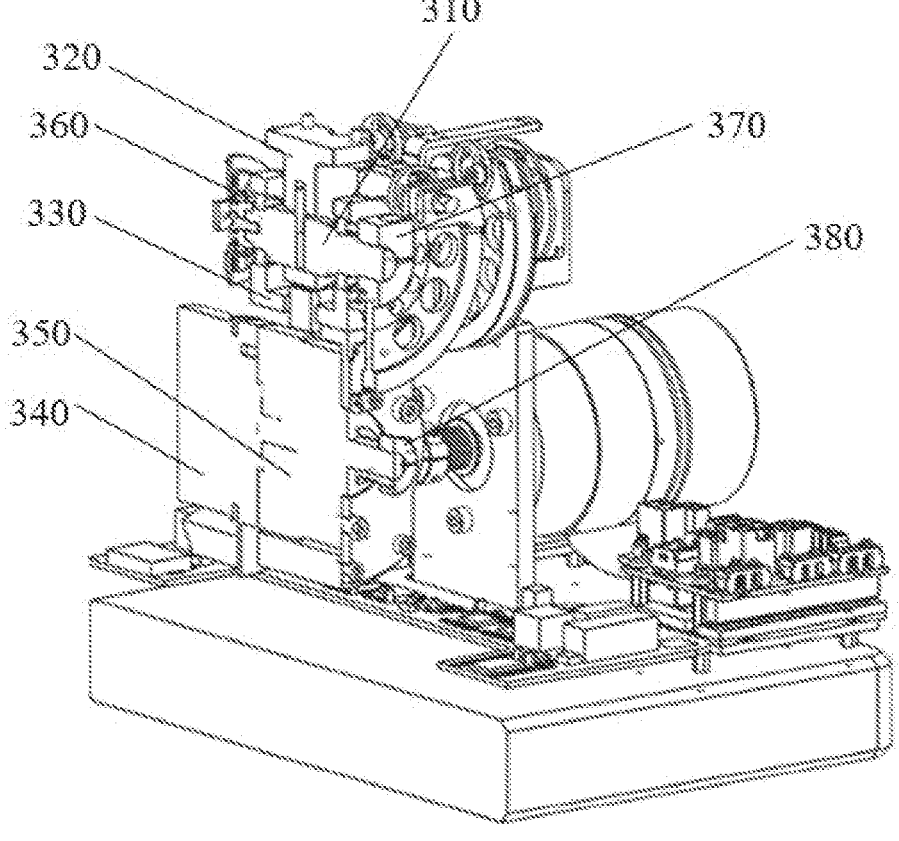
FIG. 4 is a schematic diagram illustrating a portion of an exemplary structure of a posture adjustment member according to some embodiments of the present disclosure.
Figure 5:
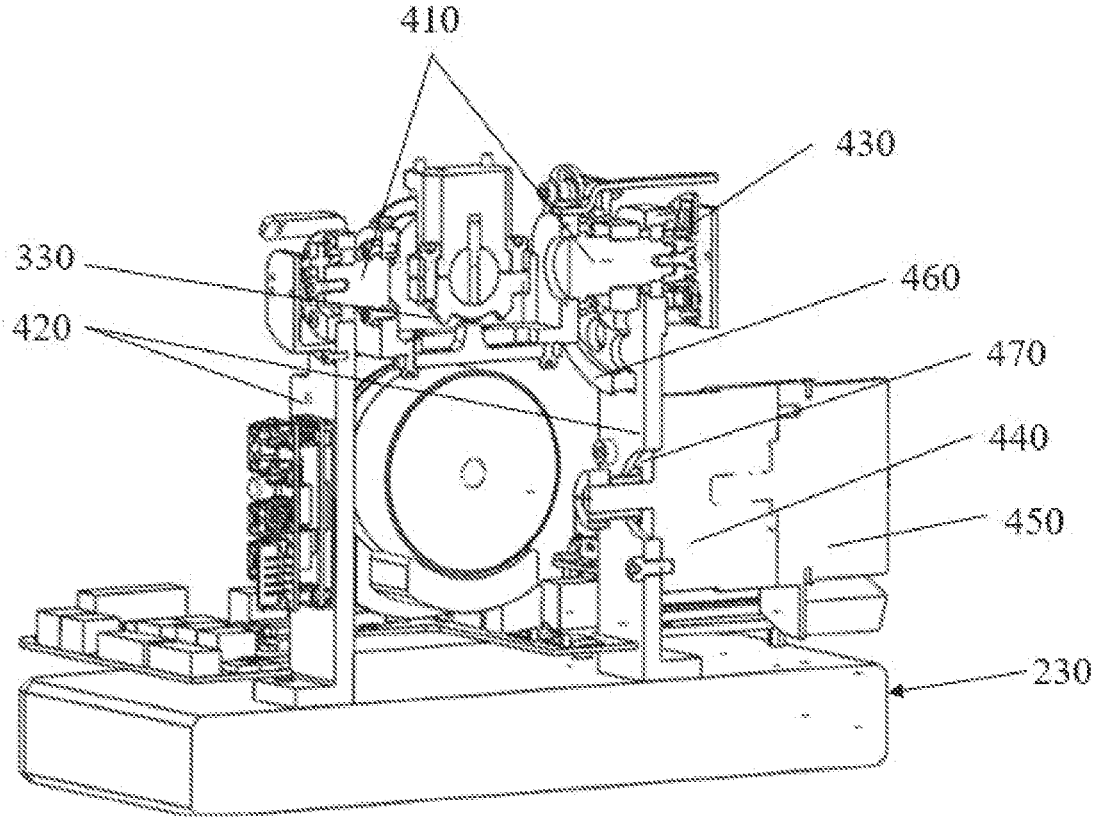
FIG. 5 is a schematic diagram illustrating a portion of an exemplary structure of a posture adjustment member according to some embodiments of the present disclosure.
Figure 6:
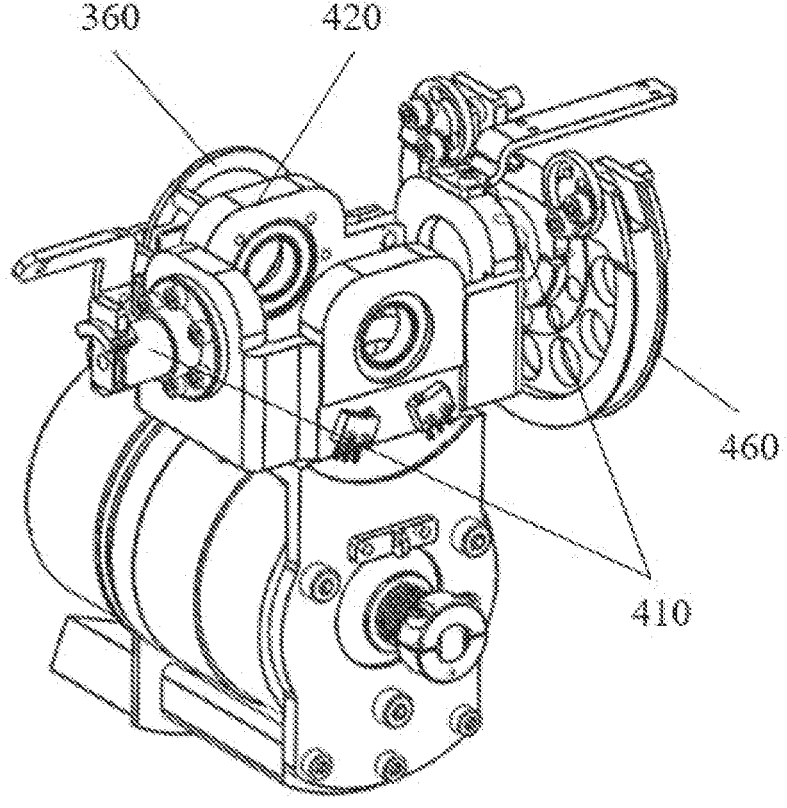
FIG. 6 is a schematic diagram illustrating a portion of an exemplary structure of a posture adjustment member according to some embodiments of the present disclosure.
Figure 7:
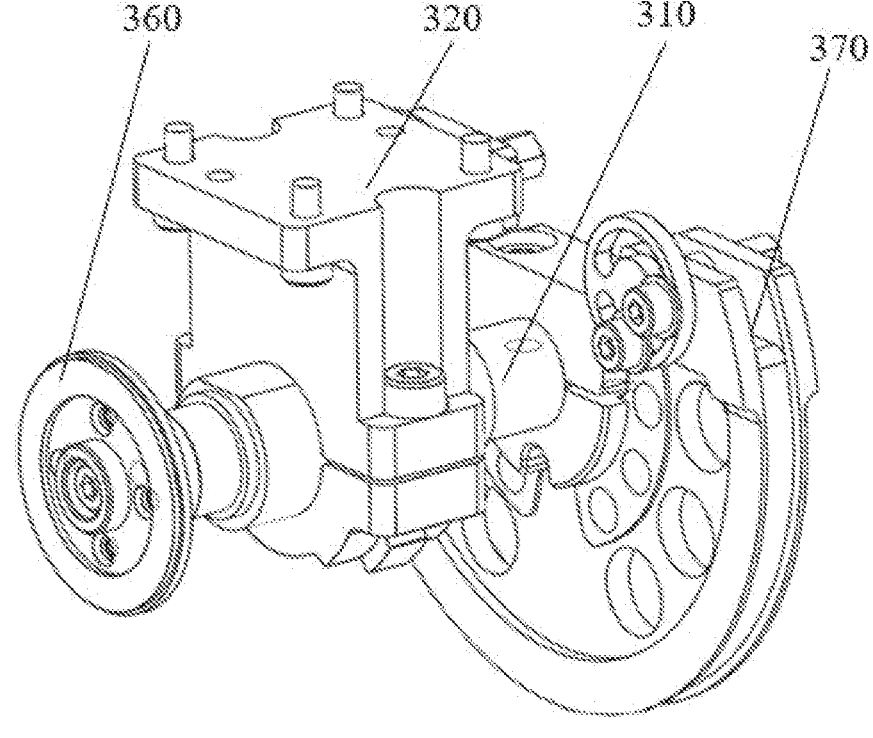
FIG. 7 is a schematic diagram of a portion of a structure of an exemplary posture adjustment member according to some embodiments of the present disclosure.
Figure 8:
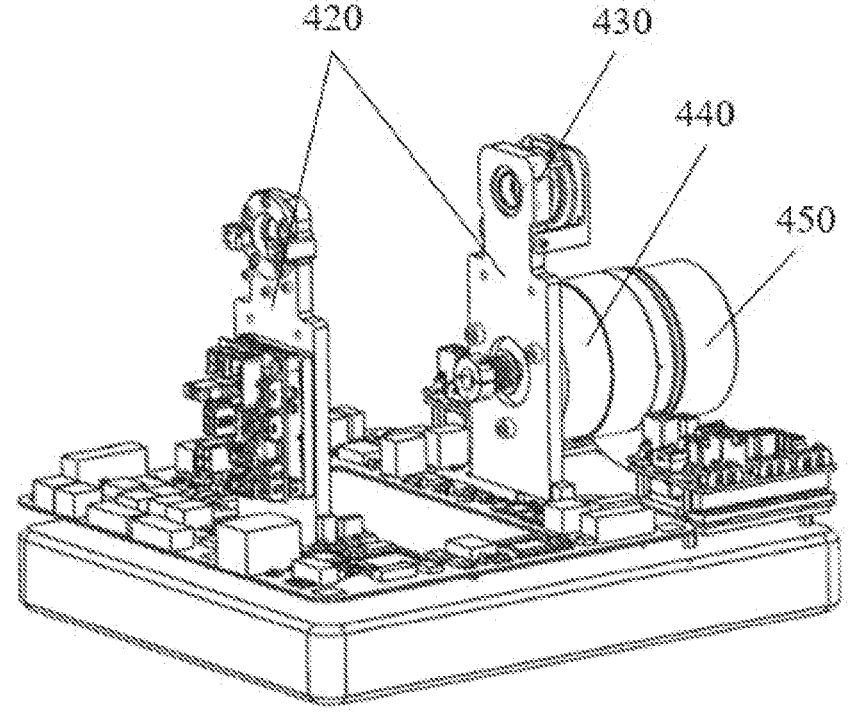
FIG. 8 is a schematic diagram of a portion of an exemplary structure of a posture adjustment member according to some embodiments of the present disclosure.

FIG. 4 is a schematic diagram illustrating a portion of an exemplary structure of a posture adjustment member 220 according to some embodiments of the present disclosure. FIG. 5 is a schematic diagram illustrating a portion of an exemplary structure of a posture adjustment member 220 according to some embodiments of the present disclosure. FIG. 6 is a schematic diagram illustrating a portion of an exemplary structure of a posture adjustment member 220 according to some embodiments of the present disclosure. FIG. 7 is a schematic diagram of a portion of an exemplary structure of a posture adjustment member 220 according to some embodiments of the present disclosure. FIG. 8 is a schematic diagram of a portion of an exemplary structure of a posture adjustment member 220 according to some embodiments of the present disclosure. Detailed descriptions of the posture adjustment member 220 illustrated in the embodiments of the present disclosure are provided below. It should be noted that the following embodiments are merely intended to illustrate the present disclosure, which are not limitations of the present disclosure thereof.

As shown in FIG. 4, in some embodiments, the first rotation mechanism may include a first rotation shaft 310, a first installation base 320, and a second installation base 330. The first rotation shaft 310 may be rotated around the rotation axis A of the first rotation mechanism with the first rotation-freedom degree. The first installation base 320 may be used to install the end control assembly 210. The second installation base 330 may be used for a rotatable installation of the first rotation shaft 310. For example, the first rotation shaft 310 may be installed on the second installation base 330 by a bearing, thereby allowing a smooth and reliable rotation of the first rotation shaft 310 and achieving a limitation by an end cover of the bearing.

In some embodiments, the end control assembly 210 is fixedly provided to the first installation base 320, and the first installation base 320 is fixedly connected to the first rotation shaft 310. A structure form of the first installation base 320 is not limited herein, as long as the first installation base 320 can be connected to the bottom of the end control assembly 210 and the first rotation shaft 310. Merely by way of example, the first installation base 320 may include two portions. The two portions may be fitted together to form a cavity for a connection of the first rotation shaft 310. Two ends of the first rotation shaft 310 may protrude from the first installation base 320 for a connection of another component or for an installation of another component.

As shown in FIG. 5, in some embodiments, the second rotation mechanism may include a second rotation shaft 410 and a third installation base 420. The second rotation shaft 410 may be rotated around the rotation axis B of the second rotation mechanism with the second rotation-freedom degree. The third installation base 420 may be used for the rotatable installation of the second rotation shaft 410. For example, the second rotation shaft 410 may be installed on the third installation base 420 by the bearing, thereby allowing a smooth and reliable rotation of the second rotation shaft 410 and achieving a limitation by an end cover of the bearing.

In some embodiments, the second rotation shaft 410 is fixedly connected to the second installation base 330. Therefore, the first rotation shaft 310 has no effect on the second rotation shaft 410 when the first rotation shaft 310 rotates in the second installation base 330. When the second rotation shaft 410 rotates, the second rotation shaft 410 drives the second installation base 330 that is fixedly connected to the second rotation shaft 410 and the first rotation shaft 310 arranged in the second installation base 330 to move. In addition, when the first rotation shaft 310 is in a locked state, that is, when the first rotation shaft 310 is unable to rotate, the first rotation shaft 310 still has no effect on the second rotation shaft 410. The rotation of the second rotation shaft 410 drives the second installation base 330 that is fixedly connected to the second rotation shaft 410 and the first rotation shaft 310 arranged in the second installation base 330 to move.

In some embodiments, an angle between a rotation axis of the first rotation shaft 310 and a rotation axis of the second rotation shaft 410 may be greater than 10°, such as any angle within a range of 10-180° (e.g., 60°, 90°, 135°, etc.). In some embodiments, the angle between the rotation axis of the first rotation shaft 310 and the rotation axis of the second rotation shaft 410 may be greater than 85°. For example, the angle between the rotation axis of the first rotation shaft 310 and the rotation axis of the second rotation shaft 410 may be 90°. In some embodiments, the rotation axis of the first rotation shaft 310 may intersect with or may not intersect with and the rotation axis of the second rotation shaft 410. When the rotation axis of the first rotation shaft 310 does not intersect with the rotation axis of the second rotation shaft 410, the first rotation shaft 310 may be provided in a space above the second rotation shaft 410.

When the rotation axis of the first rotation shaft 310 intersects with the rotation axis of the second rotation shaft 410, a plane in which the rotation axis of the first rotation shaft 310 and the rotation axis of the second rotation shaft 410 are located may or may not be parallel to a horizontal plane. As shown in FIG. 6, merely by way of example, the second rotation shaft 410 may include two shaft segments provided with a same rotation axis, i.e., a first portion and a second portion capable of rotating around a rotation axis. The first portion and the second portion are capable of rotating synchronously. The second installation base 420 may be provided between the first portion and the second portion such that the first rotation shaft 310 and the second rotation shaft 410 are located in a same plane (the rotation axis of the first rotation shaft 310 intersects with the rotation axis of the second rotation shaft 410). The first rotation shaft 310 is capable of rotating relative to the second installation base 330 to achieve the first rotation-freedom degree. The second rotation shaft 410 may be driven to rotate relative to the third installation base 420 through the first rotation shaft 310 and the second installation base 330, thereby achieving the second rotation-freedom degree.

In some embodiments, the master manipulator device 200 may further include a first information acquisition device and a second information acquisition device. The first information acquisition device may be used to detect a rotation angle of the first rotation mechanism 221 and transmit the rotation angle to the communication device 120. The second information acquisition device may be used to detect a rotation angle of the second rotation mechanism 222 and transmit the rotation angle to the communication device 120. In some embodiments, the first information acquisition device may include a first encoder 360. As shown in FIG. 7, the first encoder 360 may be provided at an end portion of the first rotation shaft 310. The second information acquisition device may include a second encoder 430. As shown in FIG. 8, the second encoder 430 may be provided at an end portion of the second rotation shaft 410.

An encoder is a device that compiles and converts signals or data into a signal form for communication, transmission, and storage. The encoder usually includes a disk and a read head, and the rotation angle may be detected through a cooperation between the disk and the read head. In some embodiments, the first encoder 360 and the second encoder 430 may be used to detect the rotation angle of the first rotation shaft 310 and the rotation angle of the second rotation shaft 410 and feedback the rotation angle to the robot body 110. The end executor 130 is controlled by the robot body 110 to adjust a spatial posture according to the rotation angle to satisfy operational requirements.

In some embodiments, the master manipulator device 200 may further include a first feedback assembly and a second feedback assembly. The first feedback assembly is used to apply a posture adjustment resistance to the first rotation mechanism 221 based on first feedback information. The second feedback assembly is used to apply a posture adjustment resistance to the second rotation mechanism 222 based on second feedback information. In some embodiments, the first feedback assembly may be connected to the end portion of the first rotation shaft 310. The first feedback assembly may include a first speed reduction assembly and a first feedback motor 340. The first feedback motor 340 may be connected to the first rotation shaft 310 via the first speed reduction assembly. The first speed reduction assembly may include a first synchronous wheel 370 and a second synchronous wheel 380. In some embodiments, the second feedback assembly may be connected to the end portion of the second rotation shaft 410. The second feedback assembly may include a second speed reduction assembly and a second feedback motor 450. The second feedback motor 450 may be connected to the second rotation shaft 410 via the second speed reduction assembly. The second speed reduction assembly may include a third synchronous wheel 460 and a fourth synchronous wheel 470. The second feedback assembly may also be provided at an end portion of the first portion of the second rotation shaft 410. The second feedback assembly may also be provided at an end portion of the second portion of the second rotation shaft 410.

The feedback assembly is a component used to apply the posture resistance. The first feedback assembly is capable of applying the posture resistance to the first rotation shaft 310 based on the first feedback information, and the second feedback assembly is capable of applying the posture resistance to the second rotation shaft 410 based on the second feedback information. The first feedback information and the second feedback information are resistance information of different directions when the end executor 130 performs the posture adjustment operation. In some embodiments, when the end control assembly 210 drives the first rotation shaft 310 to rotate, the end control assembly 210 is capable of driving the first feedback motor 340 to rotate through the first speed reduction assembly. When the end control assembly 210 drives the second rotation shaft 410 to rotate, the end control assembly 210 is capable of driving the second feedback motor 450 to rotate through the second speed reduction assembly. When the posture adjustment resistance is applied to the end executor 130, the first feedback motor 340 may receive the posture adjustment resistance. The first feedback motor 340 is capable of applying a resistance in an opposite direction of a rotation direction to the first rotation shaft 310 through the first speed reduction assembly and a resistance in an opposite direction of the rotation direction to the second rotation shaft 410 through the second speed reduction assembly to achieve force feedback. When the rotation of the end executor 130 relative to the first rotation-freedom degree is completed, the first rotation shaft 310 is capable of being locked to prevent from further rotation, thereby avoiding an influence of the rotation of the first rotation shaft 310 on the spatial posture of the end executor 130 during subsequent operations. Similarly, when the rotation of the end executor 130 relative to the second rotation-freedom degree is completed, the second rotation shaft 410 is capable of being locked to prevent from further rotation, thereby avoiding an influence of the rotation of the second rotation shaft 410 on the spatial posture of the end executor 130 during subsequent operations. More details about the locking of the rotation shaft may be found elsewhere in the present disclosure, such as the descriptions of a locking mechanism.

Merely by way of example, when the end executor 130 corresponding to the end control assembly 210 is the puncture needle, the first feedback assembly and the second feedback assembly may provide feedback on the resistance during the posture adjustment to simulate an actual posture adjustment process of the puncture needle, which is easy for the medical staff to perform operations. In some embodiments, when the posture adjustment member 220 drives the end executor 130 to adjust the spatial posture, the end executor 130 may feedback the encountered posture adjustment resistance to the robot body 110. The robot body 110 may control the first feedback assembly to apply a resistance that is equivalent to a posture adjustment resistance in a first direction to the first rotation shaft 310 based on the first feedback information. The robot body 110 may control the second feedback assembly to apply a resistance that is equivalent to a posture adjustment resistance in a second direction to the second rotation shaft 410 based on the second feedback information. In this way, the medical staff can feel the resistance in the opposite direction of the rotation direction when driving the first rotation shaft 310 to rotate, thereby achieving force feedback during the posture adjustment.

In some embodiments, the first speed reduction assembly may include the first synchronous wheel 370 and the second synchronous wheel 380. The first synchronous wheel 370 may be provided at the end portion of the first rotation shaft 310 and the second synchronous wheel 380 may be provided at an output end portion of the first feedback motor 340. The first synchronous wheel 370 is in a transmission connection with the second synchronous wheel 380. In some embodiments, the first synchronous wheel 370 and the second synchronous wheel 380 may be in a form of wheel transmission structure, gear transmission structure, etc. The transmission connection may also be achieved by a synchronous belt, a wire rope, etc., which is sleeved on the first synchronous wheel 370 and the second synchronous wheel 380. The transmission connection achieved by the synchronous belt, the wire rope, etc., may avoid an effect of a gap (e.g., a gap between gears in a gear transmission structure) of a return stroke.

In some embodiments, a radius of the first synchronous wheel 370 may be greater than a radius of the second synchronous wheel 380. For example, a ratio of the radius of the first synchronous wheel 370 to the radius of the second synchronous wheel 380 may be 6.25:1. The ratio of the radius of the first synchronous wheel 370 to the radius of the second synchronous wheel 380 is a transmission ratio, which may be determined according to a posture adjustment load.

In some embodiments, the second speed reduction assembly may include the third synchronous wheel 460 and the fourth synchronous wheel 470. The third synchronous wheel 460 may be provided at the end portion of the second rotation shaft 410 and the fourth synchronous wheel 470 may be provided at the output end portion of the second feedback motor 450. The third synchronous wheel 460 is in the transmission connection with the fourth synchronous wheel 470. In some embodiments, the transmission connection between the third synchronous wheel 460 and the fourth synchronous wheel 470 may be achieved by the synchronous belt, the wire rope, etc., which is sleeved on the third synchronous wheel 460 and the fourth synchronous wheel 470. In some embodiments, the second speed reduction assembly may also be in the form of wheel transmission structure, gear transmission structures, etc., whose principles are substantially the same as those of the synchronous belt, the wire rope, etc., which is not repeated herein.

In some embodiments, a radius of the third synchronous wheel 460 may be greater than a radius of the fourth synchronous wheel 470. For example, a ratio of the radius of the third synchronous wheel 460 to the radius of the fourth synchronous wheel 470 may be 6.25:1. The ratio of the radius of the third synchronous wheel 460 to the radius of the fourth synchronous wheel 470 is the transmission ratio, which may be determined according to the posture adjustment load.

Figure 9:
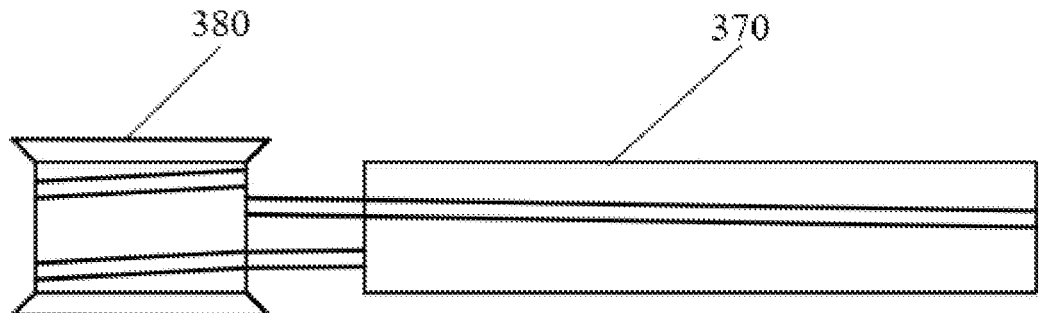
FIG. 9 is a schematic diagram illustrating a double-rope transmission according to some embodiments of the present disclosure.

FIG. 9 is a schematic diagram illustrating a double-rope transmission according to some embodiments of the present disclosure. In some embodiments, as shown in FIG. 9, the first synchronous wheel 370 may be in a double-rope transmission connection with the second synchronous wheel 380. Taking the wire rope as an example, when the transmission is achieved through a wire rope, a diameter of the wire rope needs to be increased if a transmission stiffness needs to be increased, a plain wire diameter (a diameter of a minimum unit of the wire rope) of the wire rope also needs to be increased synchronously, and the diameter of the second synchronous wheel 380 also needs to be increased synchronously (a linear relationship exists between the plain wire diameter and the diameter of the second synchronous wheel 380 to satisfy a service life), which in turn affects the transmission ratio. The double-rope transmission does not change the diameter of the second synchronous wheel 380, thereby increasing the transmission stiffness by two times while keeping the transmission ratio to be unchanged.

In some embodiments, a guiding device may be provided to guide a rope so that ropes in the double-rope transmission may be wound into the second synchronous wheel 380 according to a preset pitch during the posture adjustment process. A pitch of the rope on the first synchronous wheel 370 corresponds to a pitch of the rope on the second synchronous wheel 380.

In some embodiments, the rope may be tensioned and fixed by a tension member. For example, the tension member may be a tension bolt and a tension nut matching with the tension bolt. A working length of the rope may be adjusted by adjusting the tension member, so that the rope may work on the synchronous wheel under a suitable pressure, thereby preventing the rope from slipping in a working state.

In some embodiments, the third synchronous wheel 460 and the fourth synchronous wheel 470 may be in the double-rope transmission connection, the structure, principle, and effect of which are the same as those of the first synchronous wheel 370 and the second synchronous wheel 380, which is not repeated herein.

In some embodiments, the arrangement of the double-rope transmission may be provided with a guiding device and a tension device accordingly, the structure, principle, and effect of which are the same as the transmission between the first synchronous wheel 370 and the second synchronous wheel 380, which is not be repeated herein.

Figure 10:
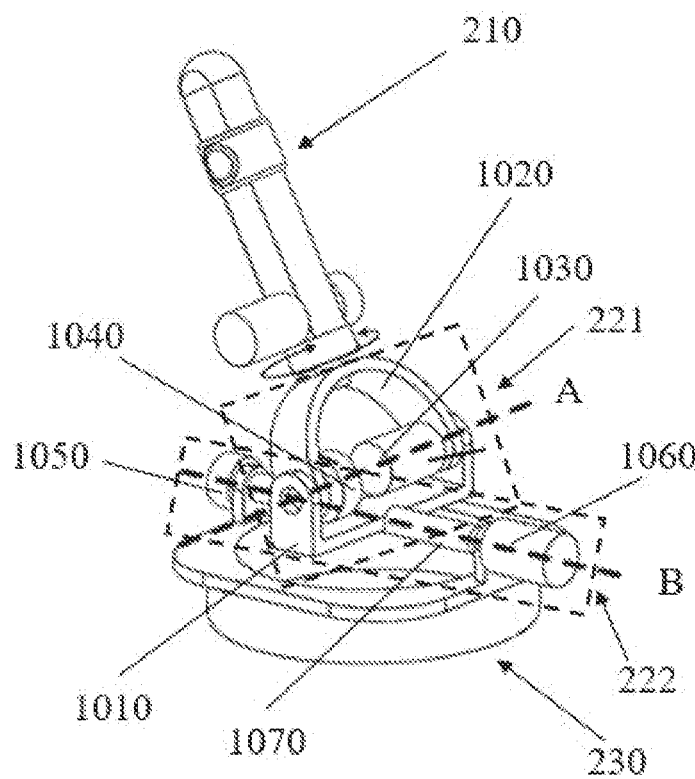
FIG. 10 is a schematic diagram illustrating another exemplary structure of a master manipulator device according to some embodiments of the present disclosure.

FIG. 10 is a schematic diagram illustrating another exemplary structure of a master manipulator device 1000 according to some embodiments of the present disclosure. Detailed descriptions of the master manipulator device 1000 in a form of another structure illustrated in the embodiments of the present disclosure are provided below. It should be noted that the following embodiments are merely intended to illustrate the present disclosure, which are not limitations of the present disclosure.

As shown in FIG. 10, the first rotation mechanism may include a posture adjustment base 1010 and a posture adjustment ring 1020. The posture adjustment base 1010 is rotatably connected to the posture adjustment ring 1020, and the posture adjustment ring 1020 is fixedly connected to the end control assembly 210. In some embodiments, the posture adjustment ring 1020 may be in a form of a semi-circular ring, and the posture adjustment base 1010 may be connected with the posture adjustment ring 1020 through a rotation pair. As shown in FIG. 10A, rotation axis of the rotation pair may coincide with the rotation axis A of the first rotation mechanism 221. A structural shape of the posture adjustment ring 1020 is not limited herein, as long as the posture adjustment ring 1020 may be rotatably installed on the posture adjustment base 1010 and fixedly connected to the bottom of the end control assembly 210.

In some embodiments, the second rotation mechanism 222 may include a third rotation shaft 1070. In some embodiments, the third rotation shaft 1070 may be rotatably provided on the base 230. The base 230 may be a structure used to install and carry the end control assembly 210 and the posture adjustment member 220. In some embodiments, the third rotation shaft 1070 may be installed by a bearing and limited by an end cover of the bearing to keep a stable rotation. In some embodiments, the third rotation shaft 1070 may be fixedly connected to the posture adjustment base 1010 to achieve the connection between the first rotation mechanism 221 and the second rotation mechanism 222, thereby allowing the end control assembly 210 to drive the second rotation mechanism 222 to rotate around the rotation axis B of the second rotation mechanism 222 through the posture adjustment ring 1020.

In some embodiments, an angle between a rotation axis of the posture adjustment ring 1020 and a rotation axis of the third rotation shaft 1070 may be greater than 10°, such as any angle within a range of 10-180° (e.g., 30°, 60°, 135°, etc.). In some embodiments, the angle between the rotation axis of the posture adjustment ring 1020 and the rotation axis of the third rotation shaft 1070 may be greater than 85°. For example, the angle between the rotation axis of the posture adjustment ring 1020 and the rotation axis of the third rotation shaft 1070 may be 90°, as shown in FIG. 5, a larger operation space for the first rotation mechanism 221 and the second rotation mechanism 222 may be acquired.

In some embodiments, the rotation axis of the posture adjustment ring 1020 may or may not intersect with the rotation axis of the third rotation axis 1070. When the rotation axis of the posture adjustment ring 1020 intersects with the rotation axis of the third rotation axis 1070, a plane in which the rotation axis of the posture adjustment ring 1020 and the rotation axis of the third rotation axis 1070 are located may or may not be parallel to the horizontal plane.

In some embodiments, the master manipulator device 1000 may also include a third information acquisition device and a fourth information acquisition device. The third information acquisition device may be used to detect the rotation angle of the first rotation mechanism 221 and transmit the rotation angle to the communication device 120. The fourth information acquisition device may be used to detect the rotation angle of the second rotation mechanism 222 and transmit the rotation angle to the communication device 120. In some embodiments, the third information acquisition device may include a third encoder 1040 and the fourth information acquisition device may include a fourth encoder 1050.

An encoder is a device that compiles and converts signals or data into a signal form for communication, transmission, and storage. The encoder may include a disk and a read head, and the rotation angle may be detected through the cooperation between the disk and the read head. In some embodiments, the third encoder 1040 may be provided along the rotation axis A of the first rotation mechanism 221 for detecting the rotation angle of the posture adjustment ring 1020. For example, the third encoder 1040 may be provided on an inner side of the posture adjustment ring 1020. In some embodiments, the fourth encoder 1050 may be provided at an end portion of the third rotation shaft 1070 for detecting the rotation angle of the third rotation shaft 1070. The third encoder 1040 and the fourth encoder 1050 may be communicatively connected to the robot body 110 via the communication device 120 respectively to achieve information interaction and feedback the detected rotation angle to the robot body 110, so that the end executor 130 may be controlled to rotate with the same angle through the robot body 110.

In some embodiments, the master manipulator device 1000 may also include a third feedback assembly and a fourth feedback assembly. The third feedback assembly may apply the posture adjustment resistance to the first rotation mechanism 221 based on third feedback information. The fourth feedback assembly may apply the posture adjustment resistance to the second rotation mechanism 222 based on fourth feedback information. In some embodiments, the third feedback assembly may include a third feedback motor 1030. The third feedback motor 1030 may be fixedly connected to the posture adjustment ring 1020 or the posture adjustment base 1010. For example, the third feedback motor 1030 may be provided along the rotation axis A of the first rotation mechanism 221 and connected to the posture adjustment ring 1020. The third feedback motor 1030 may also be provided in other positions and connected to the posture adjustment ring 1020 through a speed reduction member. Merely by way of example, the speed reduction member may include a wheel with a large diameter and a wheel with a small diameter sleeved with a synchronous belt, a wire rope, etc. The wheel with a small diameter may be provided on an output shaft of the third feedback motor 1030. The wheel with a large diameter may be provided along the rotation axis A of the first rotation mechanism 221 and fixedly connected to the posture adjustment ring 1020. A diameter of the wheel with a large diameter is different from a diameter of the wheel have with a small diameter to achieve transmission speed reduction. In some embodiments, an arrangement of the speed reduction member may be the same as the arrangement of first synchronous wheel 370 and the second synchronous wheel 380. In some embodiments, the speed reduction member may also be a gear, etc., whose principle is the same as that of the synchronous belt, the wire rope drive, etc., which is not repeated herein. In some embodiments, the fourth feedback assembly may include a fourth feedback motor 1060, and the fourth feedback motor 1060 may be fixedly connected to the third rotation shaft 1070. In some embodiments, the fourth feedback motor 1060 may be provided at the end portion of the third rotation shaft 1070. The fourth feedback motor 1060 may also be provided at another position (e.g., on the base 230) and connected to the third rotation shaft 1070 through a speed reduction member. Merely by way of example, the speed reduction member may include a wheel with a large diameter and a wheel with a small diameter sleeved with a synchronous belt, a wire rope, etc. The wheel with a small diameter may be provided on an output shaft of the fourth feedback motor 1060 and the wheel with a large diameter may be connected to the third rotation shaft 1070. A diameter of the wheel with a large diameter is different from a diameter of the wheel with a small diameter to achieve the transmission speed reduction. In some embodiments, an arrangement of the speed reduction member may be the same as the arrangement of the first synchronous wheel 370 and the second synchronous wheel 380. In some embodiments, the speed reduction member may also be a gear, etc., whose principle is the same as that of the synchronous belt, the wire rope drive, etc., which is not repeated herein.

The feedback assembly is a component used to apply a posture adjustment resistance. The third feedback assembly is capable of applying the posture adjustment resistance to the posture adjustment ring 1020 based on the third feedback information and the fourth feedback assembly is capable of applying the posture adjustment resistance to the third rotation axis 1070 based on the fourth feedback information. The third feedback information and the fourth feedback information are resistance information of different directions applied to the end executor 130 during the posture adjustment operation. When the posture adjustment resistance is applied to the end executor 130, the end executor 130 may feedback the posture adjustment resistance to the master manipulator device 1000 via the communication device 120. The third feedback motor 1030 and the fourth feedback motor 1060 are capable of receiving the third feedback information and the fourth feedback information to apply a resistance that is equivalent to the posture adjustment resistance of the end executor 130 to the posture adjustment ring 1020 and the third rotation axis 1070 respectively, thereby achieving a posture force feedback of the end executor 130. In this way, an operator can feel the resistance in an opposite direction of the rotation direction when driving the end control assembly 210 to rotate, thereby achieving a force feedback during the posture adjustment.

Figure 11:
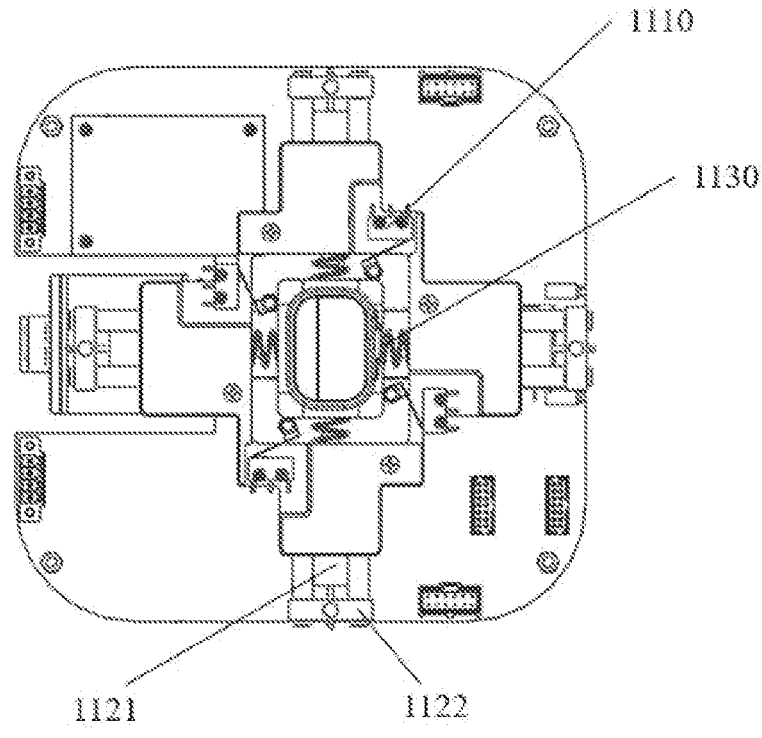
FIG. 11 is a top view illustrating an exemplary master manipulator device according to some embodiments of the present disclosure.

FIG. 11 is a top view illustrating an exemplary master manipulator device according to some embodiments of the present disclosure. As shown in FIG. 11, the posture adjustment member 220 may include a locking mechanism to lock or unlock the posture of the end control assembly 210. The end control assembly 210 is capable of moving when the locking mechanism is unlocked. In some embodiments, the locking mechanism is capable of enabling the locking and unlocking of the end control assembly 210. The locking mechanism may be fixedly provided within the posture adjustment member 220 or fixedly installed on the base 230. In some embodiments, the locking mechanism is capable of being locked and/or unlocked by contacting and/or disconnecting from the end control assembly 210. When the locking mechanism is locked, no motion can occur for the end control assembly 210 and thus the spatial posture of the end executor 130 (e.g., the puncture needle, etc.) cannot be adjusted. Specifically, the locking mechanism may lock the motion of the end control assembly 210 at two freedom degrees respectively. For example, the locking mechanism may lock the end control assembly 210 relative to the first rotation mechanism 221 and the second rotation mechanism 222 respectively. For example, the locking mechanism may cause the end control assembly 210 to be unable to rotate around the rotation axis A of the first rotation mechanism 221, thereby limiting the motion of the posture adjustment member 220 at the first rotation freedom degree. In this case, the first rotation mechanism 221 and the second rotation mechanism 222 form an integral unit with a constant relative position, and the end control assembly 210 is capable of driving the integral unit to rotate around the rotation axis B of the second rotation mechanism 222. As another example, the locking mechanism may cause the end control assembly 210 to be unable to rotate around the rotation axis B of the second rotation mechanism 222. In this case, the motion of the first rotation mechanism 221 around the rotation axis A is not affected. As another example, the locking mechanism may prevent the end control assembly 210 from rotating around the rotation axis A of the first rotation mechanism 221 and the rotation axis B of the second rotation mechanism 222. In this case, the end control assembly 210 forms a fixed unit relative to the first rotation mechanism 221 and the second rotation mechanism 222. In some embodiments, the fixed unit formed by the end control assembly 210 relative to the first rotation mechanism 221 and the second rotation mechanism 222 may rotate relative to the base 230 around a vertical line of a plane in which the base 230 is located. The rotation may be restricted by the locking mechanism. In some embodiments, the end control assembly 210 may rotate around a central axis of the end control assembly 210, and the rotation may be restricted by the locking mechanism. The locking mechanism is unlocked when the spatial posture of the end executor 130 needs to be adjusted. In this case, the end control assembly 210 is capable of moving to adjust the spatial posture of the end executor 130. When the end executor 130 is aligned with a target point, the locking mechanism may be locked so that the spatial posture of the end executor 130 does not change anymore, thereby avoid an influence of a continuous motion of the end control assembly 210 on the spatial posture of the end executor 130.

In some embodiments, the locking mechanism may include a first brake member 350 and a second brake member 440. As shown in FIG. 4, the first brake member 350 may lock and/or unlock the rotation of the first rotation mechanism 221. As shown in FIG. 5, the second brake member 440 may lock and/or unlock the rotation of the second rotation mechanism 222. The first brake member 350 and the second brake member 440 may be provided on the output shafts of the first feedback motor 340 and the second feedback motor 450 respectively. The first brake member 350 and the second brake member 440 are used to lock the output shaft of the first feedback motor 340 and/or the output shaft of the second feedback motor 450 to prevent the output shaft of the first feedback motor 340 and/or the output shaft of the second feedback motor 450 from rotating, thereby limiting the rotation of the first rotation mechanism 221 around the rotation axis A and/or limiting the rotation of the second rotation mechanism 222 around the rotation axis B. In some embodiments, the first brake member 350 and the second brake member 440 may be internal contracting brakes.

In some embodiments, the locking mechanism may include a plurality of electromagnets 1121 and a plurality of state detection units 1122 corresponding to the plurality of electromagnets 1121. The plurality of electromagnets 1121 may be provided along a peripheral side of the end control assembly 210, and the plurality of electromagnets 1121 may be connected and/or disconnected from the end control assembly 210 by powering on and/or powering off, thereby locking and/or unlocking the posture of the end control assembly 210. The plurality of state detection units 1122 may detect the states of the plurality of electromagnets 1121 and transmit the states to the communication device 120.

In some embodiments, the electromagnet(s) 1121 is capable of controlling an extension shaft abutting against the end control assembly 210 through an extension to limit the motion of the end control assembly 210. The extension and retraction of the extension shaft may be controlled by powering on or powering off the electromagnet(s) 1121. Specifically, the extension shaft may be arranged to be extended when the electromagnet(s) 1121 is powered on, or the extension shaft may also be arranged to be extended when the electromagnet(s) 1121 is powered off. The state detection unit(s) 1122 may be used to detect an operating state of the electromagnet(s) 1121, i.e., to detect whether the electromagnet(s) is powered on or powered off, so that whether the extension shaft is extended or not may be obtained accordingly. Merely by way of example, when the electromagnet(s) 1121 is powered on, the extension shaft is capable of making contact with the end control assembly 210 and limiting the rotation of the end control assembly 210 toward a direction of the extension shaft. When the electromagnet(s) 1121 is powered off, the extension shaft retracts and no longer abuts against the end control assembly 210. The restriction of the end control assembly 210 is released toward the direction of the extension shaft and the end control assembly 210 is capable of moving toward the direction in which the extension shaft is located.

In some embodiments, a count of the electromagnets 1121 is plural and the plurality of electromagnets 1121 may be evenly distributed along the peripheral side of the end control assembly 210. Merely by way of example, the count of electromagnets 1121 may be four, and the four electromagnets 1121 may be evenly distributed along the peripheral side of the end control assembly 210. The locking of the end control assembly 210 is achieved when the four electromagnets 1121 are extended. In some embodiments, the electromagnet(s) 1121 may be fixed by a component such as a thread or the like. In some embodiments, an elastic support member 1130 (e.g., a spring, etc.) may be provided on the peripheral side of the end control assembly 210. The elastic support member 1130 is capable of keeping the end control assembly 210 in a vertical state when the electromagnet(s)

1121 is in a retraction state and providing a reactive force for movement during the posture adjustment.

In some embodiments, the state detection unit(s) 1122 is capable of detecting the operating state of the electromagnet(s) 1121 in real time and feeding the operating state back to the robot body 110. A safety of a whole device may be improved under a condition that the state detection unit 1122 is capable of detecting whether the electromagnet 1121 is working properly. Merely by way of example, when the electromagnet(s) 1121 is powered off, the state detection unit(s) 1122 detects that the electromagnet(s) 1121 causes the extension shaft to be in an extended state. In this case, the state detection unit(s) 1122 feeds back a signal that the end control assembly 210 is locked to the robot body 110, which indicates that the end control assembly 210 is unable to move. When the electromagnet(s) 1121 is powered on, the state detection unit(s) 1122 detects that the electromagnet(s) 1121 causes the extension shaft to be in a retracted state. In this case, the state detection unit 1122 feeds back a signal that the end control assembly 210 is unlocked to the robot body 110, which indicates that the end control unit 210 is capable of moving. In some embodiments, the state detection unit(s) 1122 may be a photoelectric switch, or another component that enables the state detection of the electromagnet(s) 1121.

In some embodiments, the posture adjustment member 220 may further include a plurality of posture adjustment touch switches 1110, and the plurality of posture adjustment touch switches 1110 may be provided along the peripheral side of the end control assembly 210 to be used to control the locking mechanism.

In some embodiments, the posture adjustment touch switch(es) 1110 may be used to control the locking mechanism. The posture adjustment touch switch(es) 1110 may be electrically connected to the electromagnet(s) 1121, and the posture adjustment touch switch(es) 1110 is capable of controlling energizing and de-energizing of the electromagnet(s) 1110. The posture adjustment touch switch(es) 1110 may be electrically connected to the robot body 110. Merely by way of example, when the posture adjustment touch switch(es) 1110 is operated, the posture adjustment touch switch(es) 1110 is capable of powering on the electromagnet(s) 1121 so that the extension shaft controlled by the electromagnet 1121 is separated from the end control assembly 210. The end control assembly 210 is unlocked to move. When the posture adjustment touch switch(es) 1110 is operated again, the posture adjustment touch switch(es) 1110 is capable of powering off the electromagnet(s) 1121 so that the extension shaft of the electromagnet 1121 extends to lock the end control assembly 210. The locking and unlocking of the end control assembly 210 may be achieved by the powering on and powering off of the electromagnet(s) 1121.

In some embodiments, before a posture adjustment action is performed, the electromagnet(s) 1121 is unlocked by the posture adjustment touch switch(es) 1110, which controls the retraction of the extension shaft of the electromagnet(s) 1121. The end control assembly 210 may move to achieve the adjustment of the spatial posture of a functional component provided at the end of the robot arm. When the posture adjustment touch switch(es) 1110 is operated again, the extension shaft of the electromagnet 1121 is controlled to be extended and the end control assembly 210 is unable to move to avoid a false triggering of the posture adjustment action when performing actions such as surgical operations or the like. For example, when the end control assembly 210 corresponds to the end executor 130 that is the puncture needle, the rotation cannot occur during the puncture process based on clinical requirements to ensure a stable puncture process and guarantee the puncture effect. Therefore, before the puncture action is performed, the posture adjustment action is performed. After the posture adjustment action is completed, the end control assembly 210 is locked by the posture adjustment touch switch(es) 1110, and finally the puncture action is performed. In some embodiments, the posture adjustment action and the puncture action are performed in turn as long as the end control assembly 210 is unlocked before the posture adjustment action is performed and the end control assembly 210 is locked before the puncture action is performed.

In some embodiments, the posture adjustment member 220 may also include a plurality of inclination detection members (not shown in the figures). The plurality of inclination detection members may be provided along the peripheral side of the end control assembly 210. The plurality of inclination detection members may detect an inclination angle of the end control assembly 210 and transmit the inclination angle to the communication device 120. When the end control assembly 210 is inclined toward a certain direction, the inclination detection member corresponding to the direction is capable of detecting the inclination of the end control assembly 210 and then detecting the inclination angle of the end control assembly 210. The inclination detection member(s) may be electrically connected to the robot body 110. The inclination detection member(s) may feedback the inclination angle of the end control assembly 210 to the robot body 110. The robot body 110 may adjust the spatial posture of the end executor 130 according to the inclination angle, so that the end executor 130 is aligned with the target point.

In some embodiments, the end control assembly 210 may not correspond to any inclination detection member when the end control assembly 210 is a inclined state, but correspond to a position between two inclination detection members. In this case, the two inclination detection members may be used to detect the inclination angle of the end control assembly 210. A principle of the detection of the inclination angle of the end control assembly 210 by two inclination detection elements is substantially the same as that of the detection by a inclination detection element, which is not repeated herein.

Merely by way of example, a count of the inclination detection members may be four, and the four inclination detection members may be evenly distributed around the peripheral side of the end control assembly 210. The end control assembly 210 enables the spatial posture adjustment of the end executor 130 by the four inclination detection members. That is, when the end control assembly 210 moves toward any inclination detection member, the adjustment is achieved by the inclination detection member in the direction. When the end control assembly 210 also needs to move toward another direction, the end control assembly 210 moves toward another inclination detection member in the another direction.

In some embodiments, an emergency stop switch, an integral device switch, etc., may also be provided. The emergency stop switch and the integral device switch may be electrically connected to the robot body 110 respectively. The emergency stop switch may carry out an emergency stop to avoid a condition that an operation is unable to stop in an event of an accident. The integral device switch is used to energize and de-energize the device.

In some embodiments, a plurality of indicators and corresponding state indication units may also be provided, and the plurality of indicators include, but are not limited to, rotation indicators of the end control assembly 210 or the like. The state indication unit(s) may be used to control the on and off of the indicators. When the rotation indicator(s) of the end control assembly 210 is in a flashing state, the robot body 110 may receive a trigger signal, otherwise, the signal is shielded. The locking mechanism is unlocked and the state of the electromagnet(s) 1121 may be detected by the state detection unit(s) 1122, which is reported to the robot body 110. A direction of the end control assembly 210 may be identified by the inclination detection member(s) and reported to the robot body 110.

Figure 12:
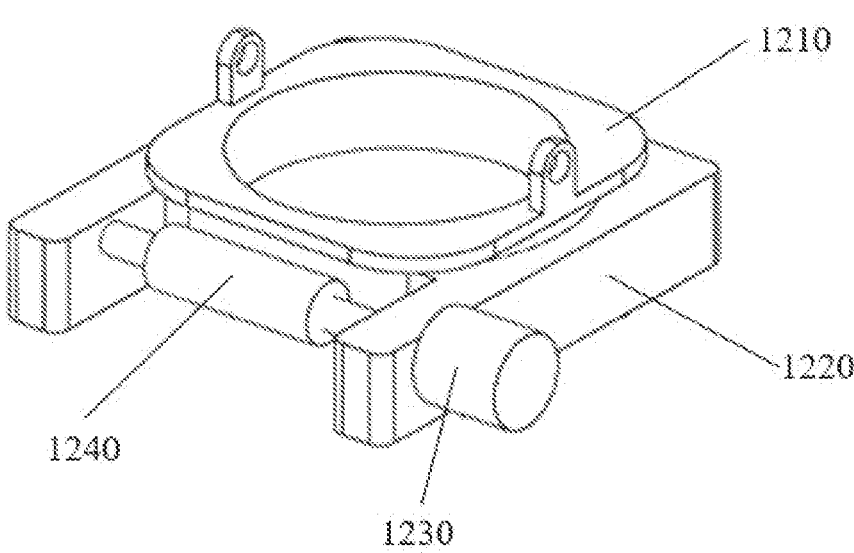
FIG. 12 is a schematic diagram illustrating an exemplary structure of a base according to some embodiments of the present disclosure.

FIG. 12 is a schematic diagram illustrating an exemplary structure of a base 230 according to some embodiments of the present disclosure. Detailed descriptions of the base 230 illustrated in the embodiments of the present disclosure is provided below. It should be noted that the following embodiments are merely intended to illustrate the present disclosure, which are not limitations of the present disclosure.

In some embodiments, the master manipulator device 200 (1000) further includes the base 230. The base 230 may be provided at the bottom of the posture adjustment member 220 for supporting and carrying. In some embodiments, the base 230 may be provided with a counterweight block with a greater mass, which does not cause the whole device to wobble during an operation, so that the whole device may keep stable. It should be noted that the base 230 may be used as a platform for supporting and carrying and applied to the master manipulator device 200, the master manipulator device 1000, and a device in a form of another structure under a condition that the base 230 is used as a base platform. Taking the master manipulator device 1000 as an example, the following descriptions are merely intended to illustrate the structure of the base 230, which are not limited herein.

In some embodiments, the base 230 may be in a form of a flat plate, to facilitate a placement on a horizontal table surface for operation. In some embodiments, the base 230 may be capable of rotating to drive the posture adjustment member 220 and the end control assembly 210 provided on the base 230 to rotate with the base 230, thereby mapping a posture adjustment plane in which a function component provided on the end portion of the robot arm is located.

In some embodiments, the base 230 may include a base body 1220 and a rotation platform 1210. An arrangement of the rotation platform 1210 allows the posture adjustment member 220 to add a freedom degree for mapping the posture of the robot. The freedom degree is capable of mapping the posture adjustment plane of the end executor 130 to enable a one-to-one mapping relationship between the master manipulator device 1000 and the robot. As shown in FIG. 12, the rotation platform 1210 may be fixedly connected to the second rotation mechanism of the posture adjustment member 220 and the rotation platform 1210 may be rotatably connected to the base body 1220. A rotation plane of rotation platform 1210 relative to the base body 1220 may be parallel to the plane in which the base body 1220 is located, and the rotation platform 1210 is associated with a motion of at least one joint of the robot. In some embodiments, the rotation plane of the rotation platform 1210 relative to the base body 1220 may be not parallel to the plane in which the base body 1220 is located, as long as a mapping relationship between the master manipulator device 1000 and at least one joint of the robot is ensured.

In some embodiments, the base body 1220 may be in a form of frame structure and the base 230 may be in a shape of square, circular, polygonal, etc., which is not limited herein. A central portion of the base body 1220 is provided with an installation space, and a dimension of the installation space may correspond to a dimension for matching the rotation platform 1210. The rotation platform 1210 may be provided in the installation space of the base body 1220 and rotatably connected to the base body 1220. The posture adjustment member 220 may be installed on the rotation platform 1210.

In some embodiments, the base 230 may also include a drive member 1230 and a transmission assembly. The drive member 1230 may be a drive member such as an electric motor or the like, that is adapted to the power required by the rotation platform 1210. The drive member 1230 may be directly connected to the rotation platform 1210 or may be connected to the rotation platform 1210 via the transmission assembly to drive the rotation platform 1210 to rotate. In some embodiments, the drive member 1230 may be in communication with the robot body 110 via the communication device 120.

In some embodiments, the transmission assembly may include a worm 1240 and a worm gear meshed with each other. The worm 1240 is connected to an output of the drive member 1230 and the worm gear is fixedly connected to the rotation platform 1210. When the drive member 1230 drives the worm 1240 to rotate, the worm gear is capable of rotating with the worm 1240 accordingly, which drives the rotation platform 1210 to rotate around a vertical line of the plane in which the rotation platform 1210 is located simultaneously. The rotation of the rotation platform 1210 adjusts an overall posture orientation of the posture adjustment member 220. That is, the direction of the rotation axis A of the first rotation mechanism 221 and the direction of the rotation axis B of the second rotation mechanism 222 may be changed. However, the angle between the rotation axis A of the first rotation mechanism 221 and the rotation axis B of the second rotation mechanism 222 remains unchanged, thereby achieving a precise control of the rotation angle between the rotation platform 1210 and the base body 1220.

In some embodiments, the transmission assembly may include a driving wheel and a driven wheel. The driving wheel and the driven wheel are sleeved with a synchronous belt. The driving wheel is connected to the output end of the drive member and the driven wheel is fixedly connected to the rotation platform. When the drive member 1230 drives the driving wheel to rotate, the driving wheel is capable of driving the driven wheel to rotate via the synchronous belt, while driving the rotation platform 1210 to rotate around the vertical line of the plane in which the rotation platform 1210 is located. In some embodiments, the transmission assembly may also be a gear, for example, as long as a connection of the drive member 1230 is achieved and the rotation platform 1210 is driven to rotate.

In some embodiments, the rotation platform 1210 may be provided with a fifth encoder. The fifth encoder detects the rotation angle of the rotation platform 1210 and transmits the rotation angle to the communication device 120. The rotation angle detected by the fifth encoder may be transmitted to the robot body 110 via the communication device 120. The robot body 110 controls a corresponding posture adjustment plane in which the overall at least one joint of the robot is located to rotate by the same angle according to the rotation angle, to achieve a synchronous change. In some embodiments, the rotation platform 1210 may be actively synchronized to the posture adjustment plane in which the at least one joint of the robot is located.

Figure 13:
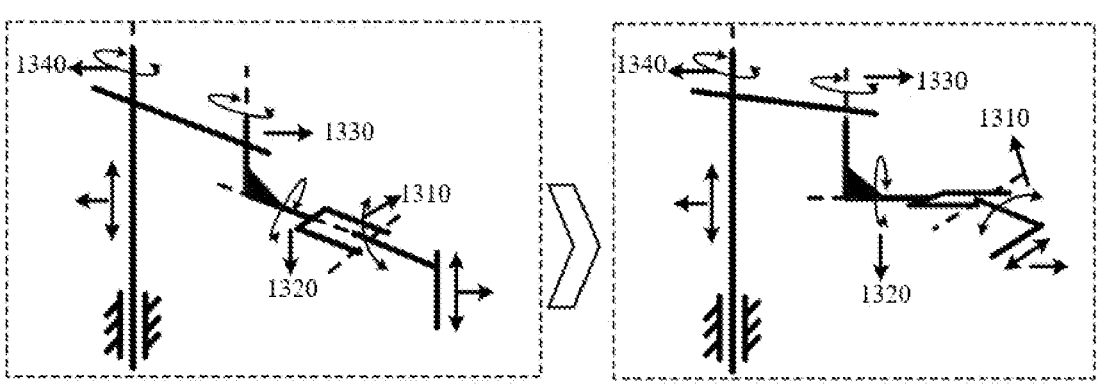
FIG. 13 is a schematic diagram illustrating a principle of multi-degree-of-freedom posture adjustment of a robot associated with an exemplary master manipulator device according to some embodiments of the present disclosure.
Figure 14:
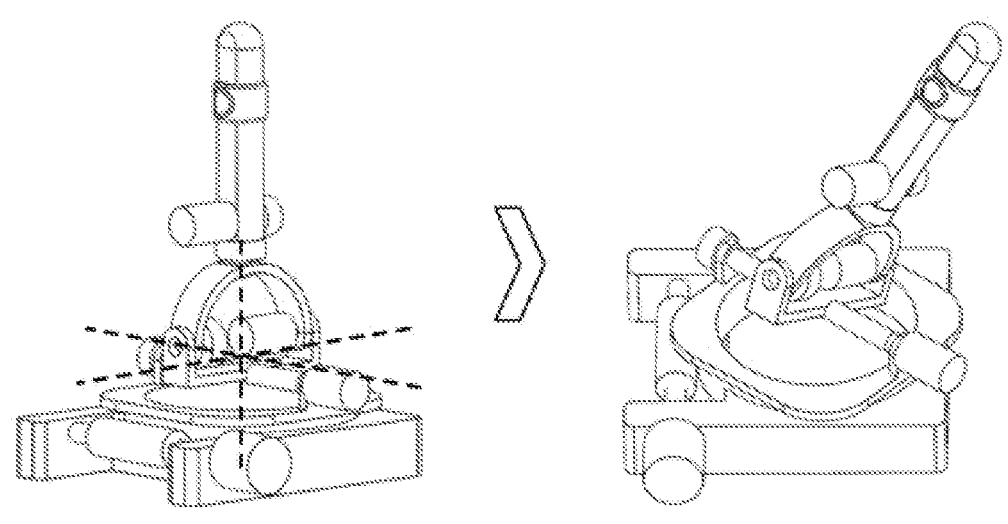
FIG. 14 is a schematic diagram illustrating a state of an exemplary master manipulator device before a posture adjustment and a state of the exemplary master manipulator device after the posture adjustment according to some embodiments of the present disclosure.

FIG. 13 is a schematic diagram illustrating a principle of multi-degree-of-freedom posture adjustment of a robot associated with an exemplary master manipulator device 1000 according to some embodiments of the present disclosure. FIG. 14 is a schematic diagram illustrating a state of an exemplary master manipulator device 1000 before a posture adjustment a state of the exemplary master manipulator device 1000 after the posture adjustment according to some embodiments of the present disclosure. Taking the master manipulator device 1000 as an example, a working principle of the master manipulator device 1000 is further described below. It should be noted that the following descriptions are intended to illustrate the working principle, which is not limit herein. A same working principle may be applied to the master manipulator device 200, which is not repeated herein.

As shown in FIG. 13, a correspondence relationship between the master manipulator device 1000 and the posture adjustment plane in which the at least one joint of the robot is located may be fed back to the robot body 110 by detecting a rotation angle of a first adjustment joint 1330 and a rotation angle of a second adjustment joint 1340 and performing a vector superposition on the two rotation angles to form rotation angle information. A control instruction is transmitted to the drive member 1230 via the communication device 120 based on the rotation angle information, so that the drive member 1230 may rotate by a corresponding angle to drive the rotation platform 1210 to rotate by the corresponding angle (a vector sum of the first adjustment joint 1330 and the second adjustment joint 1340), thereby achieving the mapping (i.e., the rotation of the rotation platform 1210 relative to the base body 1220 is associated with the motion of the at least one joint motion of the robot) of the master manipulator device 1000 to the posture adjustment plane of the robot. The process mentioned above may be performed after the posture of the robot is determined (the operator may adjust the posture freely). Under the arrangement mentioned above, the rotation freedom degree of the rotation platform 1210 relative to the base body 1220 is set up as an active mapping to the joint to achieve the same mapping as the posture of the robot without manual dragging. It should be noted that a same mapping relationship may be achieved when the base 230 is applied to the master manipulator device 200, which is not repeated herein.

The posture adjustment plane in which the posture adjustment joints of the robot are located is achieved by a vector sum of the rotation of the first adjustment joint 1330 and the second adjustment joint 1340. Posture adjustment joints of the end executor 130 correspond to the first rotation mechanism 221 and the second rotation mechanism 222 respectively. In a pre-operative preparation phase, the posture of the robot needs to be calibrated as shown in the left diagram of FIG. 13. The posture of the end of the robot arm is perpendicular to the horizontal plane, which is defined as a zero position. The posture of the master manipulator device is as shown in the left diagram of FIG. 14. Each of the posture adjustment joints of the robot (the posture adjustment joint 1310 corresponding to the first rotation mechanism 221 and the posture adjustment joint 1320 corresponding to the second rotation mechanism 222), the first adjustment joint 1330, and the second adjustment joint 1340 are adjusted as required as shown in the right diagram of FIG. 13. Posture adjustment information is recorded one by one and passed to the master manipulator device 1000. The master manipulator device 1000 controls the first rotation mechanism 221, the second rotation mechanism 222, and the base 230 to rotate by a corresponding angle (as shown in the right diagram of the FIG. 14) respectively to achieve synchronization of the posture of the joints.

As shown in FIG. 14, the master manipulator device 1000 is adjusted from a zero position state to a posture adjustment position state corresponding to the robot. The zero position of the master manipulator device 1000 is a position where a central axis of the end control assembly 210 coincides with the vertical line of the plane where the rotation platform 1210 is located. The posture adjustment plane under the zero position of the master manipulator device 1000 is parallel with the posture adjustment plane under the zero position of the robot. When the end of the robot arm changes the posture adjustment plane during a determination of the posture of the end of the robot arm, the rotation angle of the rotation platform 1210 of the master manipulator device 1000 is equal to the vector sum (the rotation angle of the first adjustment joint 1330 and the rotation angle of the second adjustment joint 1340 correspond to a positive direction and a negative (a left direction and a right direction) direction shown in FIG. 13 respectively) of the first adjustment joint 1330 and second adjustment joint 1340 of the robot. When the robot adjusts the posture adjustment joints corresponding to the first rotation mechanism 221 and the second rotation mechanism 222 during the process of determining the posture, the rotation angle information of the corresponding posture adjustment joints relative to the zero position is transmitted to the robot body 110 respectively to control the first rotation mechanism 221 and the second rotation mechanism 222 to rotate relative to the zero position by a corresponding angle. After the posture of the robot is determined, the master manipulator device 1000 achieves a one-to-one mapping relationship between the posture of the end control assembly 210 and the posture of the end executor 130 through the mapping process described above. That is, the end control assembly 210 and the end executor 130 are fully synchronized. The end executor 130 is adjusted finely according to the CT imaging through the master manipulator device 1000. It should be noted that the posture of the end control assembly 210 may also not be mapped exactly one-to-one with the posture of the end executor 130, but only partially incomplete mapping relationships may be achieved as required.

The basic concepts have been described above, apparently, for those skilled in the art, the above-mentioned detailed disclosure is only used as an example, and it does not constitute a limitation of the present disclosure. Although not explicitly described herein, various modifications, improvements, and corrections to this present disclosure may occur to those skilled in the art. Such modifications, improvements, and corrections are suggested in the present disclosure, so such modifications, improvements, and corrections still belong to the spirit and scope of the embodiments of the present disclosure.

At the same time, the present disclosure uses specific words to describe the embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it should be emphasized and noted that two or more references to "an embodiment" or "one embodiment" or "an alternative embodiment" in various places in the present disclosure are not necessarily referring to the same embodiment. Further, certain features, structures, or features of one or more embodiments of the present disclosure may be combined.

Furthermore, unless explicitly stated in the claims, the order of processing elements and sequences described in this present disclosure, the use of alphanumerics, or the use of other names is not intended to limit the order of the processes and methods of this present disclosure. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this method of disclosure does not imply that the subject matter of the description requires more features than that are recited in the claims. Rather, claimed subject matter may lie in less than all features of a single foregoing disclosed embodiment.

Some embodiments use numbers with description ingredients and attributes. It should be understood that the number described by such examples is used in some examples with the modified words "about", "approximate" or "generally" to modify. Unless otherwise stated, "about," "approximate," or "substantially" may indicate ±20% variation of the value it describes. Accordingly, in some embodiments, the numerical parameters used in the present disclosure and claims are approximations that can vary depending on the desired characteristics of individual embodiments. In some embodiments, the numerical parameters should be construed in light of a count of reported significant digits and by applying ordinary rounding techniques. Notwithstanding that the numerical fields and parameters used in some embodiments of the present disclosure to confirm the breadth of their ranges are approximations, in specific embodiments, such numerical values are set as precisely as practicable.

For each patent, patent application, patent application publication, or other materials cited in the present disclosure, such as articles, books, present disclosures, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if the description, definition, and/or terms used in the appended materials of the present disclosure is inconsistent or conflicts with the content described in the present disclosure, the use of the description, definition and/or terms of the present disclosure shall prevail.

Finally, it should be understood that the embodiments described in the present disclosure are only configured to illustrate the principles of the embodiments of the present disclosure. Other modifications may be within the scope of the present disclosure. Therefore, by way of example and not limitation, alternative configurations of the embodiments of the present disclosure may be considered consistent with the teachings of the present disclosure. Accordingly, the embodiments of the present disclosure are not limited to the embodiments explicitly introduced and described by the present disclosure.

What is claimed is:

1. A master manipulator device for a robot, comprising:
an end control assembly; and
a posture adjustment member, the posture adjustment member including a first rotation mechanism and a second rotation mechanism, the first rotation mechanism being connected to the end control assembly, the second rotation mechanism being connected to the first rotation mechanism, the end control assembly driving the first rotation mechanism to rotate around a rotation axis of the first rotation mechanism, the end control assembly driving the first rotation mechanism and the second rotation mechanism to rotate around a rotation axis of the second rotation mechanism, wherein
the first rotation mechanism includes a first rotation shaft, a first installation base, and a second installation base; the end control assembly is fixedly provided on the first installation base, the first installation base is fixedly connected to the first rotation shaft, and the first rotation shaft is rotatably provided on the second installation base; the second rotation mechanism includes a second rotation shaft and a third installation base, the second rotation shaft being rotatably provided on the third installation base, and the second rotation shaft being fixedly connected to the second installation base.

2. The master manipulator device of claim 1, wherein an angle between a rotation axis of the first rotation shaft and a rotation axis of the second rotation shaft is greater than 10°.

3. The master manipulator device of claim 1, wherein the second rotation shaft includes a first portion and a second portion that are rotatable around the rotation axis of the second rotation shaft, the first portion and the second portion being capable of rotating synchronously, the second installation base being provided between the first portion and the second portion such that the first rotation shaft and the second rotation shaft are located in a same plane.

4. The master manipulator device of claim 1, further comprising:
a first feedback assembly, configured to apply a first posture adjustment resistance to the first rotation mechanism based on first feedback information; and
a second feedback assembly, configured to apply a second posture adjustment resistance to the second rotation mechanism based on second feedback information.

5. The master manipulator device of claim 4, wherein an end portion of the first rotation shaft is connected to the first feedback assembly;
the first feedback assembly includes a first speed reduction assembly and a first feedback motor, the first feedback motor being connected to the first rotation shaft through the first speed reduction assembly;
an end portion of the second rotation shaft is connected to the second feedback assembly; and
the second feedback assembly includes a second speed reduction assembly and a second feedback motor, the second feedback motor being connected to the second rotation shaft through the second speed reduction assembly.

6. The master manipulator device of claim 5, wherein the first speed reduction assembly includes a first synchronous wheel and a second synchronous wheel, a radius of the first synchronous wheel being greater than a radius of the second synchronous wheel, the first synchronous wheel being provided at the end of the first rotation shaft, the second synchronous wheel being provided at an output end of the first feedback motor, the first synchronous wheel being in transmission connection with the second synchronous wheel; and the second speed reduction assembly includes a third synchronous wheel and a fourth synchronous wheel, a radius of the third synchronous wheel being greater than a radius of the fourth synchronous wheel, the third synchronous wheel being provided at the end of the second rotation shaft, the fourth synchronous wheel being provided at an output end of the second feedback motor, the third synchronous wheel being in the transmission connection with the fourth synchronous wheel.

7. The master manipulator device of claim 1, wherein the posture adjustment member further includes a locking mechanism.

8. The master manipulator device of claim 7, wherein the locking mechanism includes:

a first brake member, configured to lock or unlock a rotation of the first rotation mechanism; and a second brake member, configured to lock or unlock a rotation of the second rotation mechanism.

9. The master manipulator device of claim 7, wherein the locking mechanism includes a plurality of electromagnets and a plurality of state detection units corresponding to the plurality of electromagnets, the plurality of electromagnets are provided along a peripheral side of the end control assembly, and the plurality of state detection units are configured to detect states of the plurality of electromagnets and transmit the states of the plurality of electromagnets to a communication device; and wherein the plurality of electromagnets are connected to the end control assembly by energizing the plurality of electromagnets, thereby locking a posture of the end control assembly; or the plurality of electromagnets are disconnected from the end control assembly by de-energizing the plurality of electromagnets, thereby unlocking the posture of the end control assembly.

10. The master manipulator device of claim 9, wherein the posture adjustment member further includes a plurality of posture adjustment touch switches, the plurality of posture adjustment touch switches being provided along the peripheral side of the end control assembly.

11. The master manipulator device of claim 9, wherein the posture adjustment member further includes a plurality of inclination detection members, the plurality of inclination detection members being provided along the peripheral side of the end control assembly, the plurality of inclination detection members being configured to detect an inclination angle of the end control assembly and transmit the inclination angle of the end control assembly to the communication device.

12. The master manipulator device of claim 1, further comprising:

a base, the base including a base body and a rotation platform, the rotation platform being fixedly connected to the second rotation mechanism of the posture adjustment member, the rotation platform being rotatably connected to the base body, a rotation plane of the rotation platform being parallel, relative to the base body, to a plane in which the base body is located, and the rotation platform being associated with a motion of at least one joint of the robot.

13. The master manipulator device of claim 12, wherein the base further includes a drive member and a transmission assembly, the drive member driving, through the transmission assembly, the rotation platform to rotate.

14. The master manipulator device of claim 13, wherein the transmission assembly includes a worm and a worm gear meshed with each other, the worm being connected to an output end of the drive member and the worm gear being fixedly connected to the rotation platform.

15. The master manipulator device of claim 13, wherein the transmission assembly includes a driving wheel and a driven wheel, the driving wheel and the driven wheel are sleeved with a synchronous belt, the driving wheel is connected to the output end of the drive member, and the driven wheel is fixedly connected to the rotation platform.

16. A robot, comprising: a robot body, an end executor, and the master manipulator device of claim 1, wherein the end executor is connected to the robot body, the robot body is in communication with a communication device, and the master manipulator device is in communication with the communication device and the end executor.

17. The master manipulator device of claim 1, wherein the angle between the rotation axis of the first rotation shaft and the rotation axis of the second rotation shaft is greater than 85°; or the angle between the rotation axis of the posture adjustment ring and the rotation axis of the third rotation shaft is greater than 85°.

18. The master manipulator device of claim 1, wherein the rotation axis of the first rotation shaft intersects with the rotation axis of the second rotation shaft; or the rotation axis of the posture adjustment ring intersects with the rotation axis of the third rotation shaft.

19. The master manipulator device of claim 1, further comprising:

a first information acquisition device, configured to detect a rotation angle of the first rotation mechanism and transmit the rotation angle of the first rotation mechanism to a communication device; and a second information acquisition device, configured to detect a rotation angle of the second rotation mechanism and transmit the rotation angle of the second rotation mechanism to the communication device.

20. The master manipulator device of claim 19, wherein the first information acquisition device includes a first encoder, and the second information acquisition device includes a second encoder.

* * * * *